(12) United States Patent
Osher et al.

(10) Patent No.: US 8,300,971 B2
(45) Date of Patent: Oct. 30, 2012

(54) METHOD AND APPARATUS FOR IMAGE PROCESSING FOR MASSIVE PARALLEL DNA SEQUENCING

(75) Inventors: Stanley Osher, Pacific Palisades, CA (US); Bin Dong, La Jolla, CA (US); Barry Lynn Merriman, Carlsbad, CA (US)

(73) Assignee: LevelSet Systems, Inc., Pacific Palisades, CA (US)

( * ) Notice: Subject to any disclaimer, the term of this patent is extended or adjusted under 35 U.S.C. 154(b) by 457 days.

(21) Appl. No.: 12/729,147

(22) Filed: Mar. 22, 2010

(65) Prior Publication Data

US 2011/0007981 A1     Jan. 13, 2011

Related U.S. Application Data

(60) Provisional application No. 61/212,944, filed on Apr. 17, 2009.

(51) Int. Cl.
*G06K 9/40* (2006.01)
*G06K 9/32* (2006.01)
*G06K 15/02* (2006.01)

(52) U.S. Cl. .................. 382/255; 382/299; 358/1.2

(58) Field of Classification Search .......... 382/128–134, 382/254–255, 299, 305, 312, 274–276; 435/41, 435/333; 702/22; 358/1.2

See application file for complete search history.

(56) References Cited

U.S. PATENT DOCUMENTS

| 7,049,579 B2 * | 5/2006 | Ozkan et al. | 250/251 |
| 7,282,370 B2 * | 10/2007 | Bridgham et al. | 436/172 |
| 7,295,309 B1 * | 11/2007 | Morrison | 356/335 |
| 7,396,646 B2 * | 7/2008 | Quinlan et al. | 435/6.14 |
| 7,612,355 B2 * | 11/2009 | Wu et al. | 250/559.04 |
| 7,737,088 B1 * | 6/2010 | Stahler et al. | 506/30 |

* cited by examiner

*Primary Examiner* — Kanjibhai Patel
(74) *Attorney, Agent, or Firm* — Che-Yang Chen; Law Office of Michael Chen

(57) ABSTRACT

This invention relates to a method and apparatus for image processing, and more particularly, this invention relates to a method and apparatus for processing image data generated by bioanalytical devices, such as DNA sequencers. An object of the present invention is to remove artifacts such as noise, blur, background, non-uniform illumination, lack of registration, and extract pixel signals back to DNA-beads in a way that de-mixes pixels that contain contributions from nearby beads. In one aspect of the present invention, a system for optimizing an image comprises means for receiving an initial image which includes a plurality of microparticles with different intensities; a computing device, comprising a processor executing instructions to perform: generating an initial function denoting each microparticle's location and intensity in the initial image; determining an image processing operator adapted to determine an extent of point spread and blurriness in the initial image; computing an optimum function denoting each microparticle's location and intensity in an optimizing image; and producing the optimizing image with enhanced accuracy and density of the microparticles.

19 Claims, 19 Drawing Sheets

METHOD AND APPARATUS FOR IMAGE PROCESSING FOR MASSIVE PARALLEL DNA SEQUENCING

CROSS-REFERENCE OF RELATED APPLICATION

This application claims priority under 35 USC §119(e) to U.S. Provisional Patent Application Ser. No. 61/212,944, filed on Apr. 17, 2009, the entire contents of which are hereby incorporated by reference.

FIELD OF THE INVENTION

This invention relates to a method and apparatus for image processing, and more particularly, this invention relates to a method and apparatus for processing image data generated by bioanalytical devices, such as DNA sequencers.

BACKGROUND OF THE INVENTION

The combined work of Avery et al, in 1944, and Watson and Crick in 1953, established that DNA contains the information that defines each organism, and that it is a long string of chemical building blocks—denoted by the letters A, T, C, G,—whose precise order, or "sequence", is ultimately how this information is encoded. Since that point, it has been a major goal to develop ways to read this sequence, in order to eventually understand how it relates to the properties of different species, and of individuals within each species.

In 1978, Sanger introduced the first practical biochemical technique for determining the sequence of DNA. This method was refined and automated, and was the basis for all practical DNA sequencing performed in the next 25 years, culminating in the publicly funded International Human Genome Project (and the privately funded parallel effort undertaken by Celera Corporation), which in 2003 produced a reference DNA sequence for the almost 3 billion letters long human genome. This effort required nearly a decade, and billions of dollars in equipment, labor and chemical reagents. Because the Sanger reaction is inherently serial, with each reaction producing only a few hundred letters of sequence, roughly about 100 million individual reactions had to be performed in the course of this effort, ultimately using thousands of semi-automated sequencing machines, each of which could perform thousands of separate reactions per day. Since the genomes of most species are large (tens of millions to billions of letters), Sanger sequencing to determine a reference sequence for a new species, or to obtain the sequence of a specific individual within a species, remains a massive and costly undertaking, even with all the technologically improvements made during the course of the Human genome Project.

Starting in the early 1990's, new approaches to sequencing DNA were under development with the intent of overcoming fundamental limitations of the Sanger technique that made it both inherently serial and difficult to miniaturize in order to reduce reagent usage. The general goal of these methods was to make DNA sequencing massively parallel, so that millions, or billions, of DNA sequences were read at the same time within a single small reaction volume, thus allowing the large amount of sequence present in typical genomes (millions to billions of letters) to be read quickly, and at greatly reduced cost in terms of labor and chemical reagents.

More recently, several such massively parallel sequencing platforms have been developed to the commercial level, including the 454 system (Roche, 2004), the Solexa system (Illumina, 2005), the SOLiD system (ABI/Life Technologies, 2006), the HelioScope system (Helicos, 2007), the Polinator system (Danaher Motion, 2008), and others are presently under development, such as the systems at Complete Genomics, Inc., Intelligent BioSystems Inc., and Pacific Bio, Inc. While the Sanger technique remains the gold standard for sequencing in terms of accuracy and read length, these new technologies have rapidly become the preferred method of generating the large amounts of DNA sequence necessary for sequencing of new organisms, or for sequencing individuals, for the purpose of finding individual sequence variations relative to the species reference sequence. In particular, this latter activity will be a key component of personalized medicine, where an individual patient's DNA sequence will be factored into their medical treatment.

A variety of biochemical processes are conducted in current massively parallel sequencers, and one feature they have in common is that they all acquire primary data in the form of millions of digital images, each image showing a field filled with many localized "spots" or "beads." These images must be processed to extract the bead locations and bead brightness signals which are converted to the DNA sequence information by rules appropriate for the specific platform. However, as shown in FIG. 1, the beads are usually very small, blurred and densely clustered, and it may be difficult to determine the location and signal strength of the beads. Under these circumstances, the results of DNA sequencing may be adversely affected.

Therefore, there remains a need for a new and improved method and apparatus for processing image data generated by bioanalytical devices, such as DNA sequencers, to optimize the image with enhanced resolution, accuracy and bead density.

SUMMARY OF THE INVENTION

It is an object of the present invention to provide a method and apparatus for image optimization in bioanalytical processes, such as DNA sequencing, to improve the speed and accuracy of the resulting image data, wherein the signals from the image can be more accurately extracted by demixing the signals from or within image pixels, so that the signals are more properly assigned to the DNA fragments.

It is another object of the present invention to provide a method and apparatus to enable different types of DNA sequencers to increase their sequencing production rate (up to four times) without otherwise modifying the hardware, optics, electronics or chemistry of the sequencing system.

It is still another object of the present invention to provide a method and system for image optimization utilizing level set and partial differential equation (PDE) based methods to find the "best fit" between an initial image and an optimum image.

It is a further object of the present invention to provide a method and system for image optimization which can be used in different platforms, such as systems having (1) precise characteristics of the spots in the images, (2) partially or fully ordered spatial arrays of spots, or (3) a number of color channels.

It is still a further object of the present invention to provide a method and system for image optimization to correct certain artifacts that interfere with image processing, such as removal of noise and blurriness in images, as well as the removal of background, including non-uniform illumination effects, and registration of images that may be spatially misaligned due to imperfections in the optical or robotic components of the system.

According to one aspect of the present invention, an image optimization method comprises the steps of receiving an initial image which includes a plurality of microparticles with different intensities; generating an initial function denoting each microparticle's location and intensity of the initial image; determining an image processing operator adapted to determine an extent of point spread and blurriness in the initial image; computing an optimum function denoting each microparticle's location and intensity of an optimizing image; and producing the optimizing image with enhanced resolution, accuracy and density of said microparticles according said optimum function, wherein the image processing operator is adapted to transform the optimum function to a modified optimum function, and when the difference of pixel values between the modified optimum function and the initial function is smaller than a predetermined threshold, the optimizing image is formed.

In one embodiment, the step of receiving an initial image includes the step of removing background in said initial image. In another embodiment, the step of generating an initial function denoting each microparticle's location and intensity of the initial image may include the step of locating the microparticles in the initial image; collecting images derived from scattered or focused light from said microparticles; determining approximate center of each microparticle; and correlating said sequence of said optical signals with the locations of said microparticles.

In still another embodiment, the step of generating an initial function denoting each microparticle's location and intensity of the initial image may further include the step of communicating with an image capture device within a processor to retrieve the initial image.

In a further embodiment, the step of computing an optimum function denoting each microparticle's location and intensity of the optimizing image may include the step of incorporating a weight function to provide location information of the microparticles. In a different embodiment, the step of computing an optimum function denoting each microparticle's location and intensity of the optimizing image includes the step of inverting the extent of point spread or blurriness in the initial image.

In an exemplary embodiment, an $l_1$-minimization model $$\min_u \left\{ \|\mu u\|_1 + \frac{1}{2\delta}\|u\|^2 \text{ s.t. } \|Au - f\| \le \varepsilon \right\}$$

may be applied to find the optimum function which denotes each microparticle's location and intensity in the optimizing image.

According to another aspect of the present invention, a system for optimizing an image comprises: means for receiving an initial image which includes a plurality of microparticles with different intensities; a computing device, comprising a processor executing instructions to perform: generating an initial function denoting each microparticle's location and intensity of the initial image; determining an image processing operator adapted to determine an extent of point spread and blurriness in the initial image; computing an optimum function denoting each microparticle's location and intensity of an optimizing image; and producing the optimizing image with enhanced accuracy and density of the microparticles, wherein the image processing operator is adapted to transform the optimum function to a modified optimum function, and when the difference of pixel values in the modified optimum function and the initial function is smaller than a predetermined threshold, the optimizing image is formed.

In one embodiment, the means for receiving an initial image includes means for removing background in said initial image. In a different embodiment, generating an initial function denoting each microparticle's location and intensity of the initial image includes locating the microparticles in the initial image; collecting images derived from scattered or focused light from said microparticles; determining approximate center of each microparticle; and correlating said sequence of said optical signals with the locations of said microparticles.

In another embodiment, generating an initial function denoting each particle's location and intensity of the initial image further includes communicating with an image capture device within a processor to retrieve the initial image.

In a further embodiment, computing an optimum function denoting each particle's location and intensity of the optimizing image includes incorporating a weight function to provide location information of the microparticles. In still a further embodiment, computing an optimum function denoting each particle's location and intensity of the optimizing image includes inverting the extent of point spread or blurriness in the initial image.

According to an exemplary aspect, a method for optimizing an image including a plurality of analytes anchored to a plurality microparticles, comprises the steps of: receiving an initial image including a plurality of said analytes anchored to a plurality of microparticles and optically detectable labels attaching to said analytes, wherein when exposing said microparticles to radiation, a sequence of optical signals are generated; generating an initial function denoting each microparticle's location and signal intensity of the initial image; determining an image processing operator; computing an optimum function denoting each microparticle's location and signal intensity of an optimizing image; and producing the optimizing image with enhanced resolution and density of said microparticles, wherein the image processing operator is adapted to transform the optimum function to a modified optimum function, and when the difference of pixel values between the modified optimum function and the initial function is smaller than a predetermined threshold, the optimizing image is formed. In one embodiment, the analytes may be oligonucleotides or nucleic acid molecules.

The present invention together with the above and other advantages may best be understood from the following detailed description of the embodiments of the invention illustrated in the drawings below.

BRIEF DESCRIPTION OF THE DRAWINGS

FIGS. 6a to 6c illustrate an experiment testing the mathematical model in the present invention, wherein FIG. 6a is the synthetic image (blurred) with artificial beads, FIG. 6b is the deblurred image, and FIG. 6c shows the ground truth.

FIGS. 7a to 7d illustrate another experiment testing the mathematical model in the present invention, wherein FIG. 7a is the synthetic image (blurred) with artificial beads, FIGS. 7b and 7c are the deblurred image with constant and variant $\mu$, respectively, and FIG. 7d shows the ground truth.

FIGS. 8a to 8c illustrate another experiment testing the mathematical model in the present invention, wherein FIG. 8a is the synthetic image (blurred) with artificial beads, FIG. 8b is the deblurred image with constant $\mu$, and FIG. 8c is the deblurred image with variant $\mu$.

FIGS. 9a to 9c illustrate another experiment testing the mathematical model in the present invention, wherein FIG. 9a is the synthetic image (blurred) with artificial bead location, FIG. 9b is the deblurred image with variant $\mu$, and FIG. 9c is the ground truth.

FIGS. 10a to 10c depict the result of background removal, wherein FIG. 10a shows the original image, FIG. 10b shows background removal image, and FIG. 10c illustrates background.

FIGS. 11a to 11c depict the result of background removal of a focal map image, wherein FIG. 11a shows the original image, FIG. 11b shows background removal image, and FIG. 11c illustrates background.

FIGS. 12a to 12d illustrate the result of registration (between image f and g), wherein FIGS. 12a to 12c depict the result when at least one image is blurred, and FIG. 12d illustrates the result when both images are deblurred.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 1:
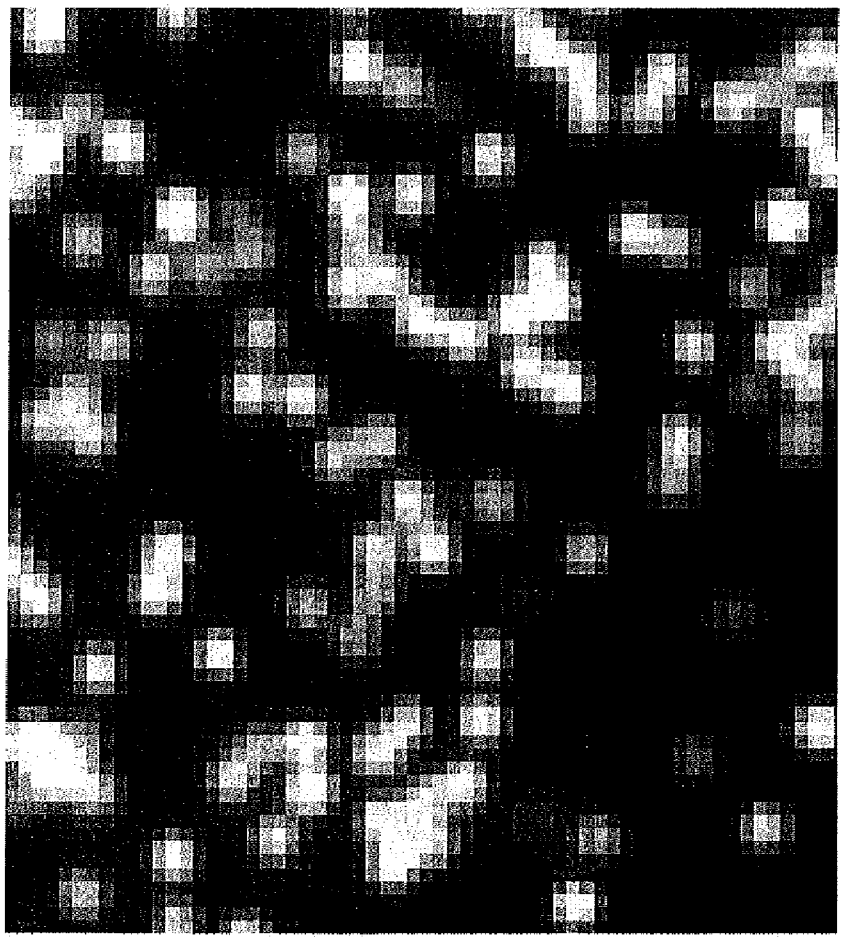
FIG. 1 illustrates an image produced by the ABI SOLiD system: a small portion of a real 2048×2048 pixel image from the ABI SOLiD system, showing approximately 100 beads.

This invention relates to a method and apparatus for image processing, and more particularly, this invention relates to a method and apparatus for processing image data generated by DNA sequencers. As stated above, current massively parallel DNA sequencers all acquire primary data in the form of millions of digital images, each image showing a field filled with many small and densely clustered "spots." These images would be processed to extract the spot locations and spot brightness signals which are converted to the DNA sequence information by rules appropriate for the specific platform. As shown in FIG. 1, it may be difficult to determine the location and signal strength of the small and densely clustered spots, which may adversely affect the result of DNA sequencing.

Figure 2:
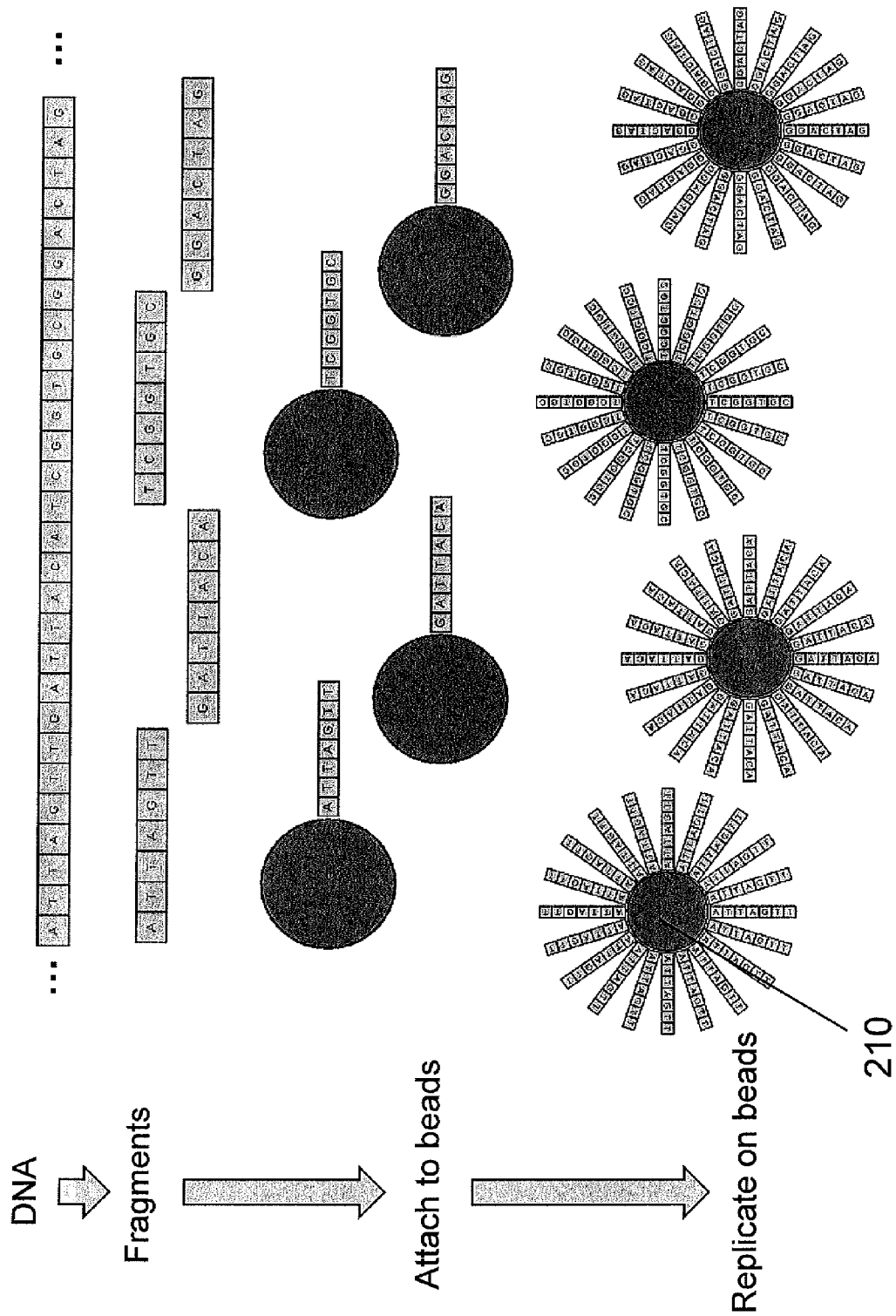
FIG. 2 illustrates a specific example of conducting a massively parallel DNA sequencing in the ABI SOLiD system: the DNA to be sequenced in fragmented into a pool of short fragments, which are then exposed to billions of microscopic beads, and processed so that a random fragment attaches to each bead and covers the bead with many copies of the initial fragment.
Figure 2A:
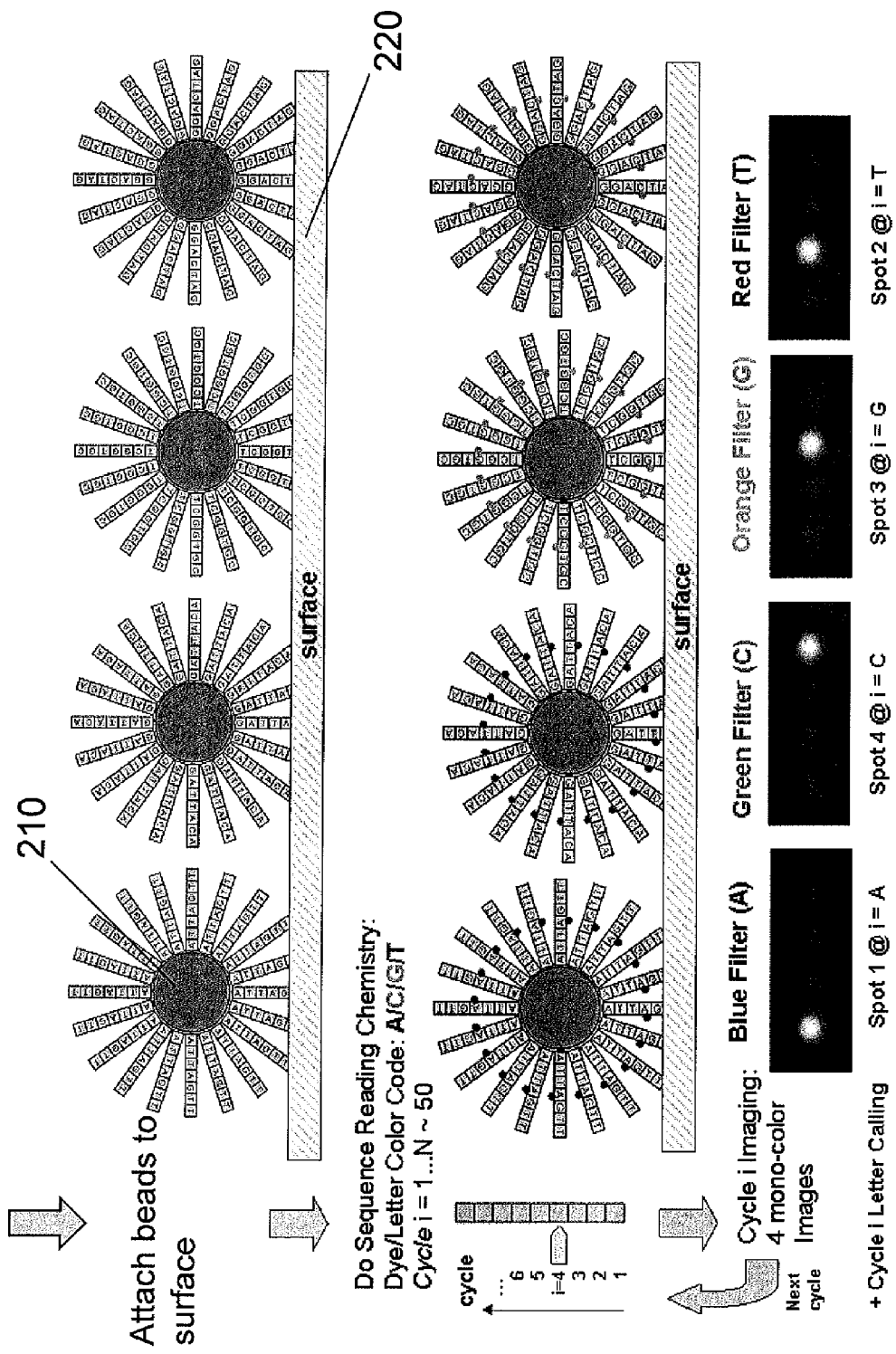
FIG. 2a illustrates the next step continuing from FIG. 2: the DNA-carrying beads are immobilized onto a microscope slide surface, covered with a gasket that allows chemical reagents to be pumped in and out, and then undergo a series of chemical reactions which report sequence information in the form of a 4-color signal, which can be captured as microscope images of the slides.
Figure 2B:
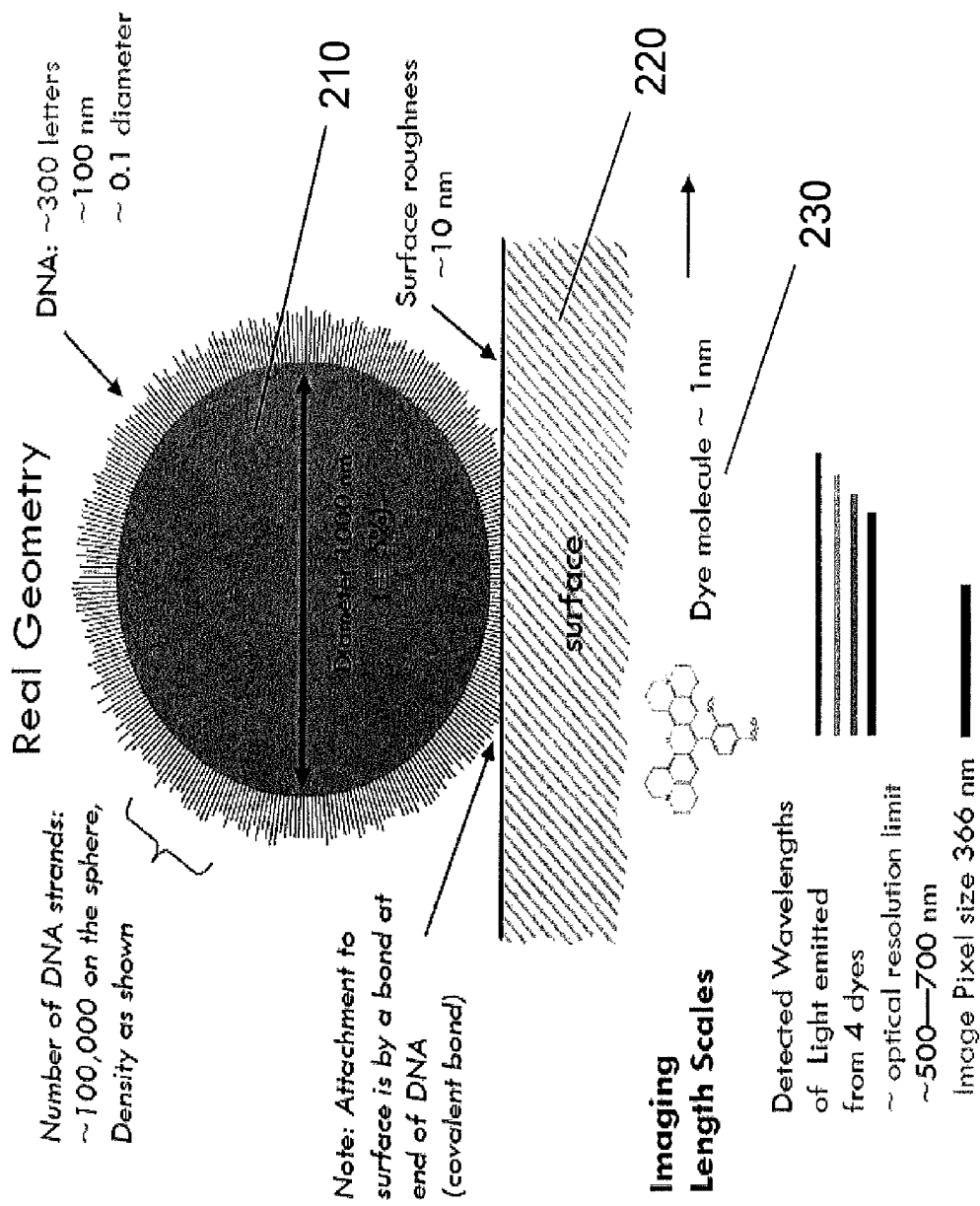
FIG. 2b illustrates the real geometry of the DNA strands clustered on the beads.
Figure 2C:
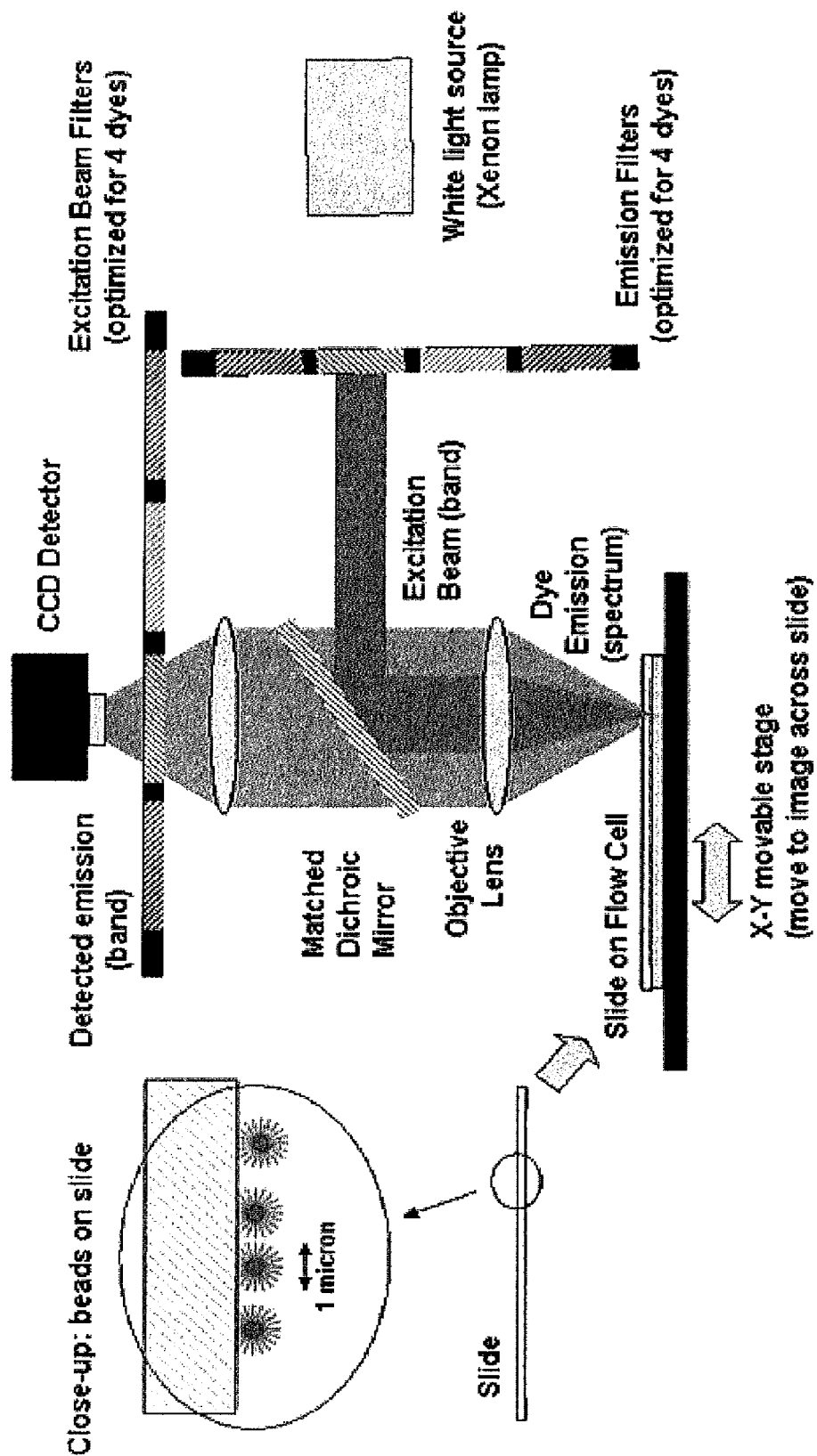
FIG. 2c illustrates a schematic imaging system and its relation to the DNA spots on the slide (the step continuing from FIG. 2a), wherein the entire slide, which may contain millions of DNA-carrying beads, each reporting via a fluorescent dye optical signal resulting from the chemical processing, is imaged by a 4-color scanning imaging system, which visits about 2500 distinct locations to acquire images that collectively cover the entire slide area.
Figure 2D:
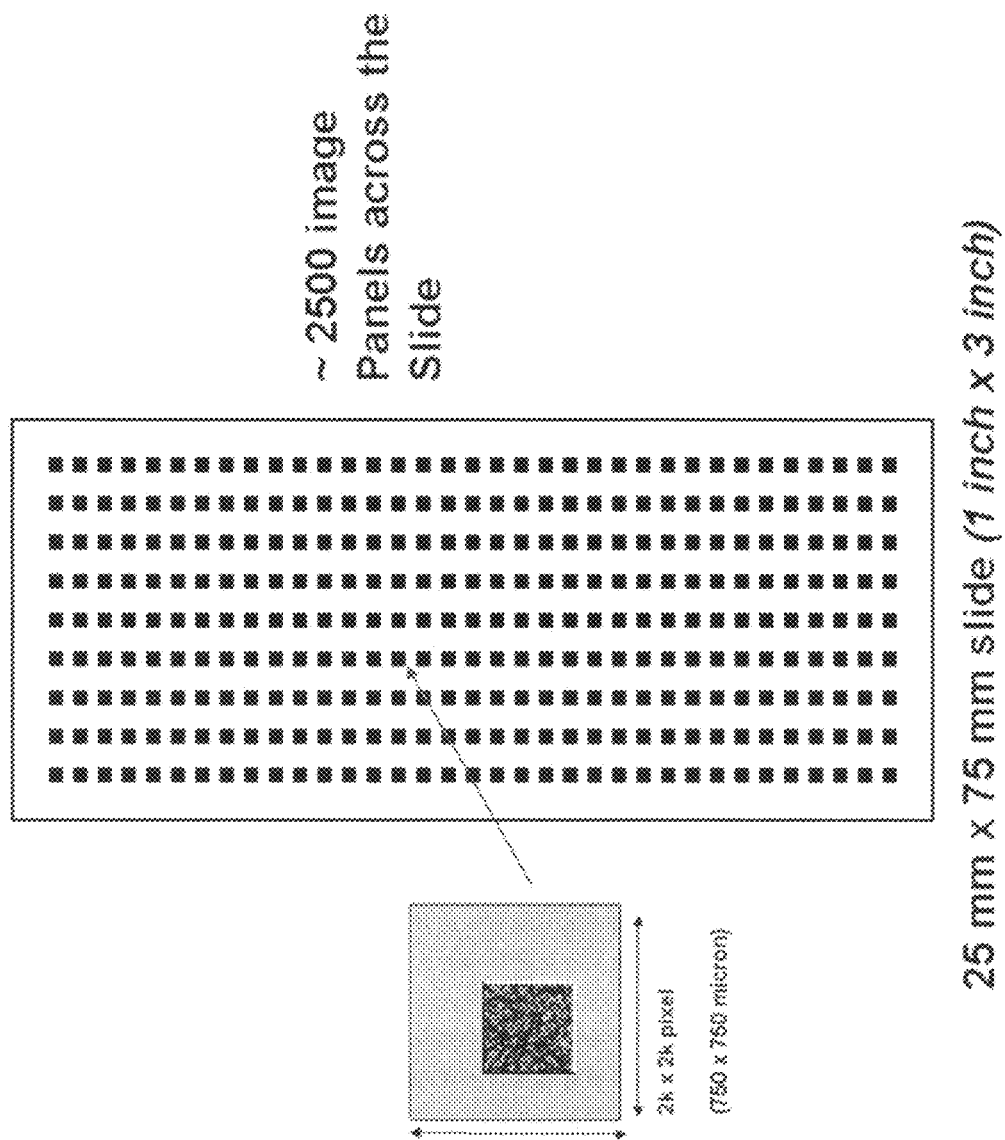
FIG. 2d depicts a schematic layout of images that cover the entire slide; each image may include 100,000 to 1,000,000 beads, which will appear as bright spots in the images, due to the fluorescent dyes deposited on each bead in the previous chemistry cycle.
Figure 2E:
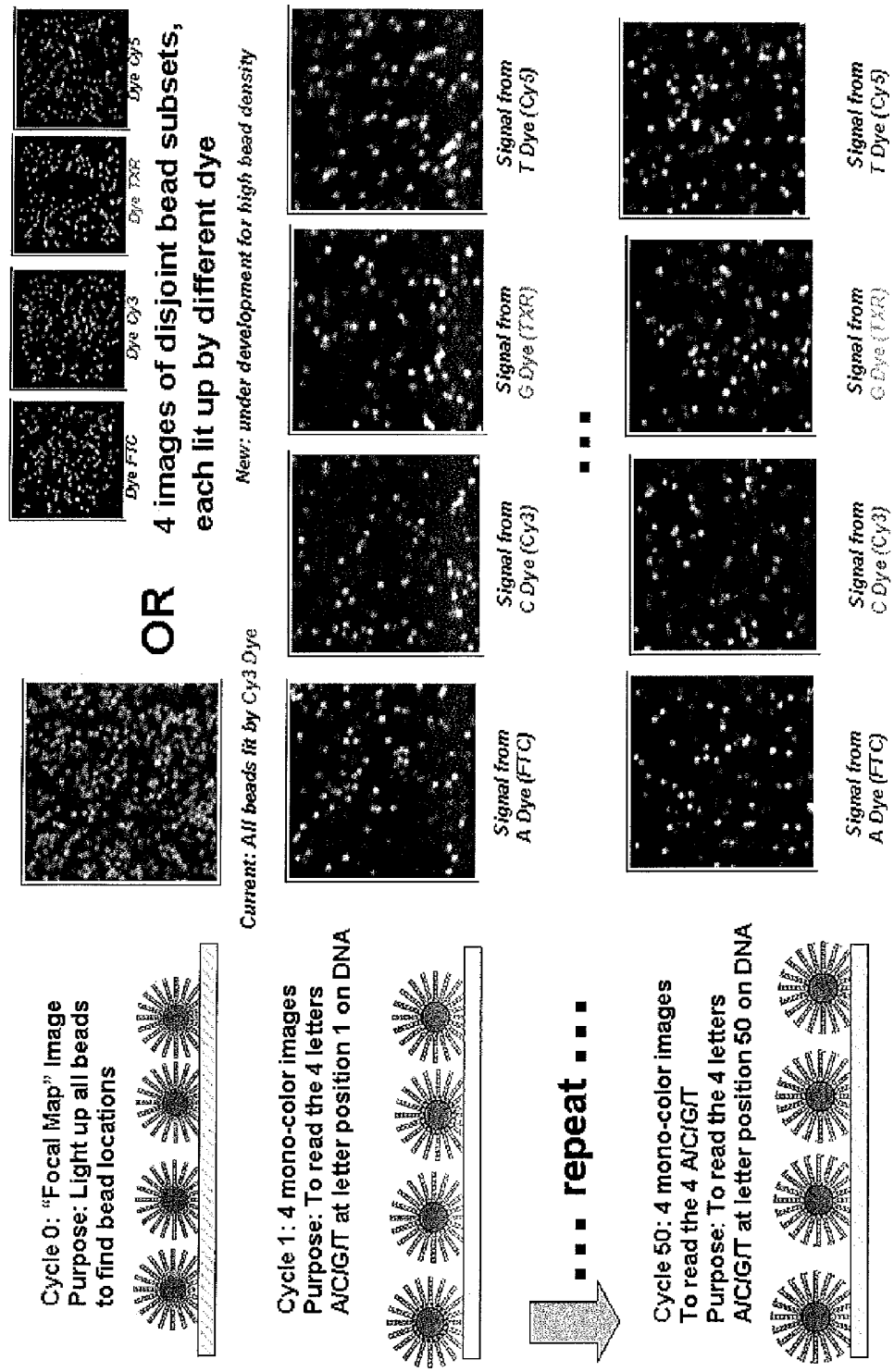
FIG. 2e depicts the cycles of chemical reactions systematically deposit 4 different dyes on the beads, such that the dye corresponds to information about the sequence.

To further understand the present invention, a DNA sequencing process using ABI SOLiD platform is depicted in FIGS. 2-2e. It is noted that the image optimization method illustrated in the present invention can be used in all other DNA sequencing platforms which produce primary data in the form of digital images.

Referring to FIG. 2, the DNA to be sequenced is first isolated by standard means from blood or saliva, and then fragmented into billions of short sequences, several hundred letters long. These fragments are randomly attached to specially derivatized microscopic plastic beads, and undergo a reaction in which each fragment is replicated many times on its host bead, so that each bead has about 100,000 copies of the original DNA fragment, and typically each such bead carries a distinct sequence. The DNA-laden beads 210 are then deposited onto a derivatized glass microscope slide 220, where they are fixed in place and remain immobile on the surface for the rest of the processing. The slide 220 is covered by a micro-fluidic gasket to form a "flow cell" that allows small volumes of chemical reagents to be pumped in out, for the purpose of chemical processing, which occurs in cycles as shown in FIG. 2a, and each cycle reports on the status of the DNA sequence in a systematic order, starting at the first location and moving outward, using fluorescent dye emissions as reporter signals, with different dye colors providing information on the underlying four possible DNA sequence letters (A, T, C, G) at each position along the fragment.

According to the real geometry of the bead 210 and the surface 220 in FIG. 2b, the bead 210 has about 100,000 DNA strands densely clustered on its sphere along with dye molecules (about 1 nm each) attaching to each nucleotide in the DNA strand. In addition, there may be millions of beads 210 on the surface 220. Under these circumstances, it may be difficult not only to locate the beads 210, but also to precisely detect and identify the signal emitted by the dye molecules which represents the DNA sequence letters.

During this chemical processing, the flow cell is also mounted into an imaging system as depicted in FIG. 2c, and CCD images are used to record the reporter signals from the dyes. Four different combinations of excitation filters, dichroic mirrors and emission filters are used to define four different color channels for the imager that allow the four dyes to be distinguished. The slide is covered with up to millions of beads, each of which will show up as a spot occupying a few pixels in an image, as indicated in FIG. 1, which shows a small portion of one such image in a specific area. A number of images are required to effectively image the entire surface of the slide, as illustrated in FIG. 2d, so that in the course of an entire run of the SOLiD 3 system, in which 100 cycles of chemistry may occur, a total of 2 million "DNA spot" images, each of which is a 4 mega pixel image, are produced during a run of the DNA sequencer in about fourteen days.

FIG. 2e summarizes how the collection of images relates to the underlying DNA sequencing chemistry. Typically, an initial image called a "focal map" is made, with the intent to light up all beads so that they can be readily located on the slide, establishing a "bead map". In practice, this may stain all beads with the same dye, or using several dye/bead types to make each image less cluttered. After the focal map is established, the sequencing chemistry cycles take place, in which the 4 dyes are reporting on the underlying sequence residing on each bead. In each monochrome CCD image, the DNA-beads show up as spots, a few pixels in extent, and thus the general character of the images is of a field of hundreds of thousands of small spots, similar in size and shape, but varying in overall signal intensity. When the density of DNA sequence information is high, meaning the DNA-bead density is high, the corresponding spot density is high and the spots become difficult to detect, recognize and distinguish.

Processing the millions of images resulting from one machine run is a massive computational challenge, and is also central to extracting the DNA sequence information from the raw image data. Specifically, this requires properly locating the DNA-carrying beads in each image, determining their identity within the total set of beads on the slide, and assigning to each bead in each image its contribution to the observed pixel signals. When beads are near each other, as shown in FIG. 1, their pixel images overlap, which makes determining bead identity difficult. Moreover, the signals accumulated in a given pixel may be due to photons emitted from several beads, and these signals may have to be demixed and properly assigned back to the source DNA-beads in order to properly sequence each DNA-bead. Aside from the signals from nearby beads obscuring and mixing with each other, the images may be beset with artifacts such as noise, blur, extraneous background signal, lack of registration, and non-uniform illumination, which must be corrected for to produce accurate results.

As noted above, while the SOLiD system outlined in detail above is used to illustrate the DNA sequencing process, the present invention can be utilized in all other massively parallel sequencing system produce similar "DNA spot" images, which require similar processing steps and face the same challenges when the spot density is high. In other systems, the source of the "spot" in the image is not many identical DNA fragments bound to a bead, it may be, for example, a single DNA fragment tethered to a surface, or a single or many identical DNA fragments in solution phase inside a microwell, or a cluster of many identical DNA fragments bound to a surface, or a DNA nano-ball of identical DNA fragments deposited on a surface, etc. Also, the imaging system need not be identical to the one described here, it could employ different optical microscopy techniques like TIRF, nearfield imaging, or Zero-Mode Waveguides, or different detectors such as CMOS instead of CCD, or it could involve non-optical imaging techniques such as Atomic Force Microscopy or Electron Microscopy. The precise form in which the underlying DNA exists, and the precise manner in which the image is formed, do not substantially impact the present invention or its utility. The essential common feature is that the image data consist of many small spots, each spot being a reporter of sequence-determining information for an underlying DNA sequence. The spots could also be randomly arranged, or partially ordered, or in a fully ordered pattern.

The present invention is adapted to provide a means and method for locating the bead positions, in a focal map and subsequent images, registering images across cycles of chemistry processing, removing artifacts such as noise, blur, background, non-uniform illumination, lack of registration, and extracting pixel signals back to DNA-beads in a way that de-mixes pixels that contain contributions from nearby beads.

The present invention is directed to a method for formulating an image processing problem as an optimization problem, where the initial image containing the beads can be defined as f(x), an optimizing image indicating the locations and intensities of the beads can be defined as u, and an image processing operator can be defined as A (mathematical definition is illustrated as below). In other words, the present invention is to find the "best fit" of bead locations and intensities, where Au≈f.

More specifically, the beads can be located and restored via $l_1$-minimization, which is known to denoise spike-like data well (S. Osher, M. Burger, D. Goldfarb, J. Xu, and W. Yin. An iterative regularization method for total variation based image restoration. *Multiscale Model. Simul*, 4(2):460-489, 2005, which is incorporated herein by reference), to remove outliers (S. Alliney. Digital filters as absolute norm regularizers. IEEE Trans. Signal Process., 40, 1548-4562, 1992, which is incorporated herein by reference), and to sparsify the results (W. Yin, S. Osher, D. Goldfarb, and J. Darbon. Bregman iterative algorithms for compressed sensing and related problems. *SIAM J. Imaging Sciences* 1(1)., pages 143-168, 2008, which is incorporated herein by reference). A standard $l_1$-minimization problem can be described as:

$$\min_u \left\{ \|\mu u\|_1 + \frac{1}{2\delta}\|u\|^2 \text{ s.t. } \|Au - f\| \le \varepsilon \right\} \tag{1}$$

where A is a convolution matrix, $\mu$ represents a weight function, and $\delta$ is a constant. Furthermore, $\|\mu u\|_1$ denotes the weighted sum of the absolute pixel values with weight $\mu$, and $\|\ \|$ denotes the $l_2$ norm, which is defined as the square root of the sum of the squares of the pixel values.

If the beads are modeled as convolution of u with some function $h(x) \in [0, 1]$ with max $h(x)=1$, and the blur is the convolution of a Gaussian kernel $g(x)$ with $h*u$, then $$Au = g*(h*u) = (g*h)*u = GHu$$

In one embodiment, the convolution kernel A=GH can be decomposed when the features of the beads and the blur are known. Furthermore, the abovementioned $l_1$-minimization problem can be solved via linearized Bregman iterations. In other embodiments, the $l_1$-minimization problem can also be solved by Bregman iterations via fix point continuation (W. Yin, S. Osher, D. Goldfarb, and J. Darbon Bregman iterative algorithms for compressed sensing and related problems. *SIAM J. Imaging Sciences* 1(1)., pages 143-168, 2008; E. Hale, W. Yin, and Y. Zhang. A fixed-point continuation method for _1-regularization with application to compressed sensing. CAAM Technical Report TR07-07, Rice University, Houston, Tex., 2007, which are incorporated herein by reference).

The linearized Bregman iterations are as follows:

$$v^{k+1} = v^k - A^T(Au^k - f) \quad (2)$$

$$u^{k+1} = \delta \cdot \text{shrink}(v^{k+1}, \mu) \quad (3)$$

where the function "shrink($v^{k+1}$, $\mu$)" is defined as follows:

$$\text{shrink}(x, \mu) := \begin{cases} x_{ij} - \mu_{ij}, & \text{if } x_{ij} > \mu_{ij} \\ 0, & \text{if } -\mu_{ij} \leq x_{ij} \leq \mu_{ij} \\ x_{ij} + \mu_{ij}, & \text{if } x_{ij} < -\mu_{ij} \end{cases}$$

where the threshold $\mu$ (which is also the weight function stated above) is a spatially variant, which can be an important factor when certain patterns of beads are known.

Figure 3:
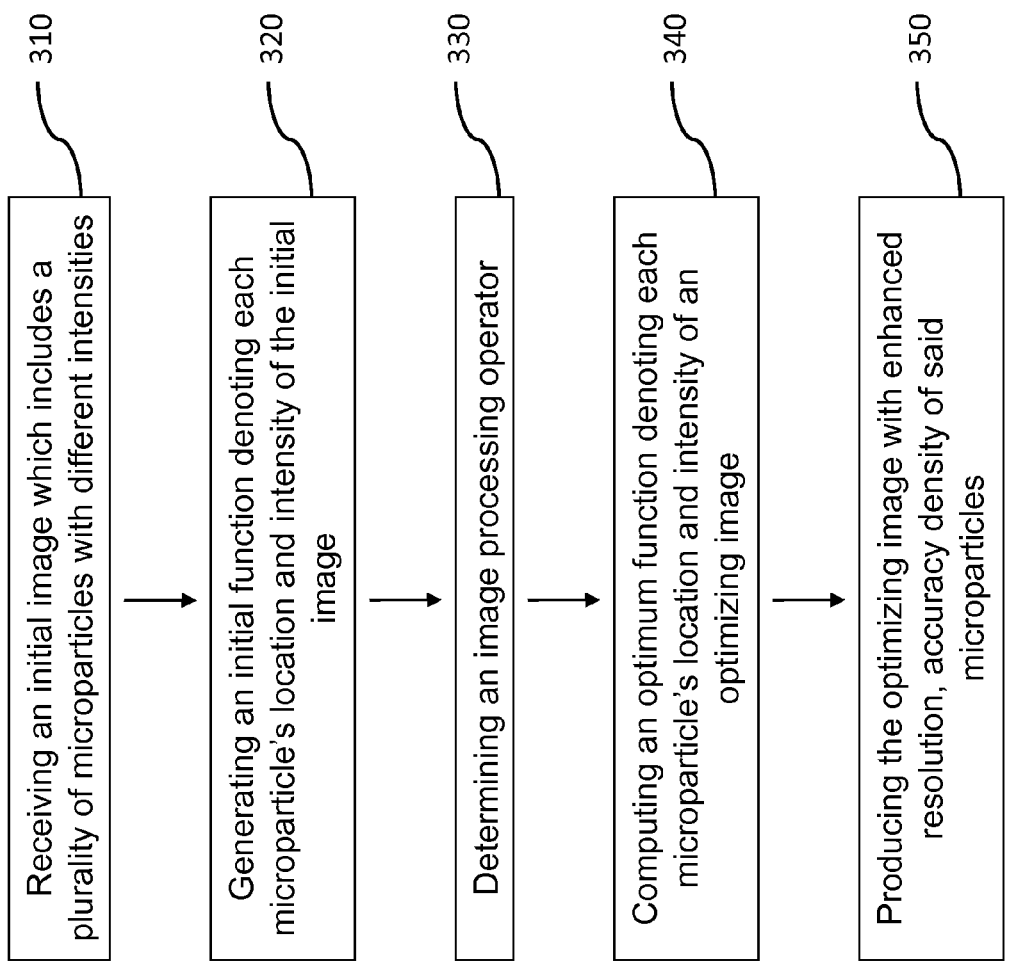
FIG. 3 depicts one aspect in the present invention, illustrating an image optimization method for generating an image with enhanced resolution and density of the microparticles.

According to one aspect illustrated in FIG. 3, an image optimization method comprises the steps of: receiving an initial image which includes a plurality of microparticles with different intensities 310; generating an initial function denoting each microparticle's location and intensity of the initial image 320; determining an image processing operator adapted to determine an extent of point spread and blurriness in the initial image 330; computing an optimum function denoting each microparticle's location and intensity of an optimizing image 340; and producing the optimizing image with enhanced resolution, accuracy and density of said microparticles 350, wherein the image processing operator is adapted to transform the optimum function to a modified optimum function, and when the difference of pixel values between the modified optimum function and the initial function is smaller than a predetermined threshold, the optimizing image is formed.

Figures 11A, 11B, 11C:
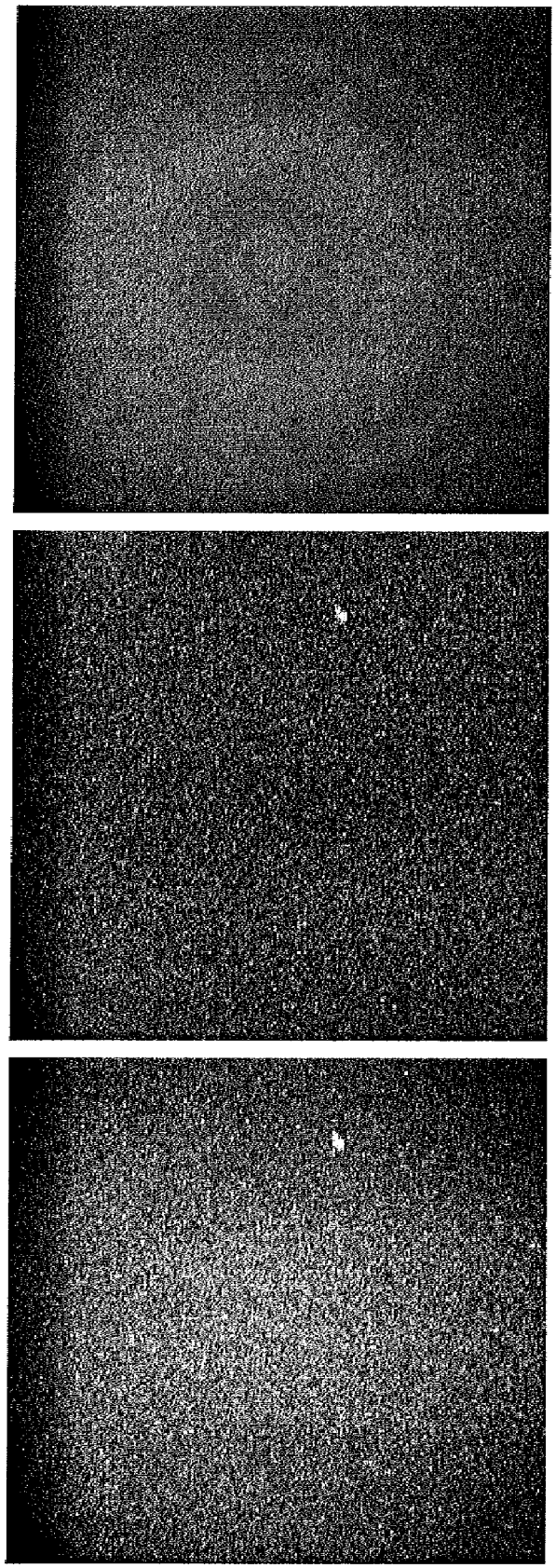

In one embodiment, the step of receiving an initial image 310 includes the step of removing background in said initial image. Since some background may exist in the image, background removal is necessary before processing the image. For example, FIG. 11a depicts an original image, and a mathematical model (5) (described below) may be applied to generate a background removal image FIG. 11b by removing the background shown in FIG. 11c.

Figure 3A:
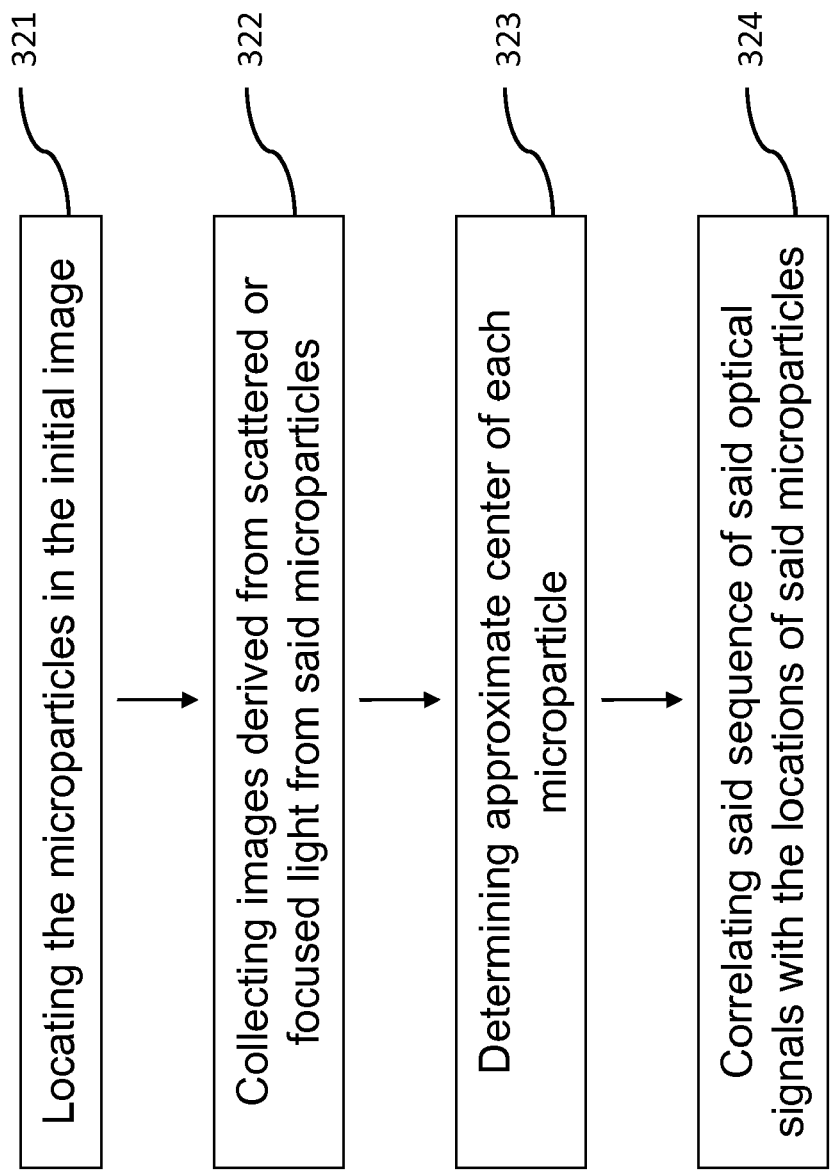
FIG. 3a illustrates one embodiment of the present invention shown in FIG. 3.

In another embodiment depicted in FIG. 3a, the step of generating an initial function denoting each microparticle's location and signal intensity of the initial image 320 includes the step of locating the microparticles in the initial image 321; collecting images derived from scattered or focused light from said microparticles 322; determining approximate center of each microparticle 323; and correlating said sequence of said optical signals with the locations of said microparticles 324. In one embodiment, the initial image is a focal map image shown in FIG. 2e, which is used for lighting up all microparticles to find the locations thereof.

Figure 7D:
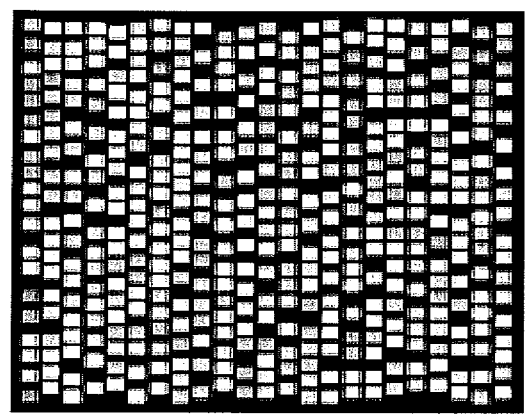
Figure 7C:
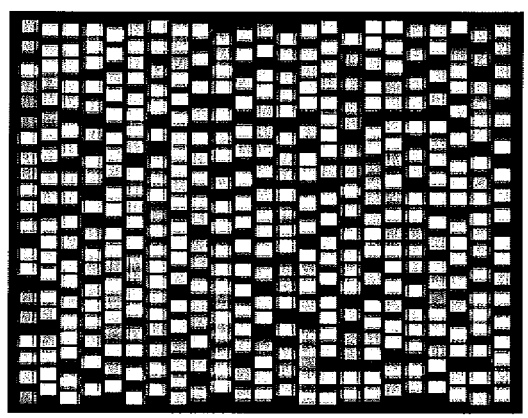
Figure 7B:
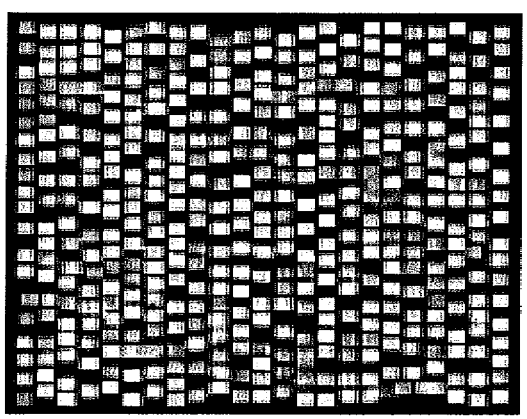

In a further embodiment, the step of computing an optimum function denoting each microparticle's location and intensity of the optimizing image 340 includes the step of incorporating a weight function provide location information of the microparticles. The effect of the weight function (also called spatially variant) may not be obvious when the microparticles' locations are, for example, along some horizontal axes as shown in FIGS. 7b and 7c. However, when the pattern of the microparticles is arbitrary as shown in FIG. 8a, incorporating the weight function can significantly improve the deblurring results, as illustrated in FIGS. 8b (with constant $\mu$) and 8c (with spatially variant $\mu$).

In still a further the step of computing an optimum function denoting each microparticle's location and intensity of the optimizing image 340 includes the steps of finding said optimum function u in the $l_1$-minimization model (1), and determining and inverting the extent of point spread or blurriness in the initial image.

In another aspect of the present invention, a system 400 for optimizing an image comprising an initial image receiver 410; a computing device 420 comprising a processor 421 executing instruction to perform generating an initial function denoting each microparticle's location and intensity of the initial image; determining an image processing operator adapted to determine an extent of point spread and blurriness in the initial image; computing an optimum function denoting each microparticle's location and intensity of an optimizing image; and producing the optimizing image with enhanced resolution, accuracy and density of the microparticles, wherein the image processing operator is adapted to transform the optimum function to a modified optimum function, and when the difference of pixel values in the modified optimum function and the initial function is smaller than a predetermined threshold, the optimizing image is formed.

In one embodiment, the initial image receiver 410 may include a background removing unit 411 for removing background in said initial image, wherein a TV-$L_1$ model $$\min_{v \in R^2} \left\{ \int |\nabla v| + \lambda \|f - v\|_1 \right\} \quad (4)$$

(described below) may be applied to implement the background removal. In another embodiment, model $$\min_{v \in R^2} \left\{ \int |\nabla v|^2 + \frac{\mu}{2} \|f - v\|^2 + \lambda(v - f) \right\} \quad (5)$$

(described below) may be applied.

Figure 4:
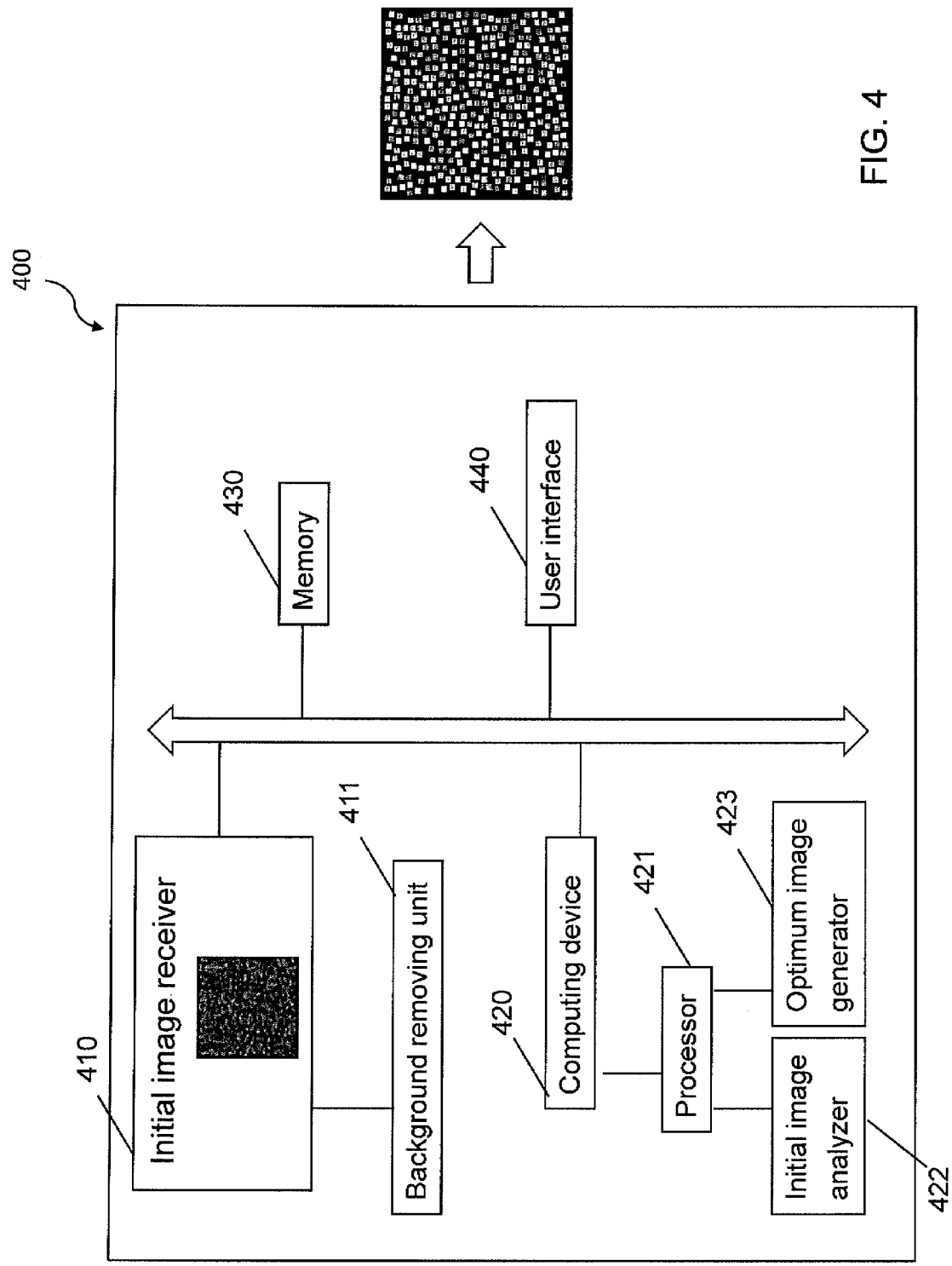
FIG. 4 depicts another aspect in the present invention, illustrating an image optimization system for generating an image with enhanced resolution, accuracy and density of the microparticles.
Figure 4A:
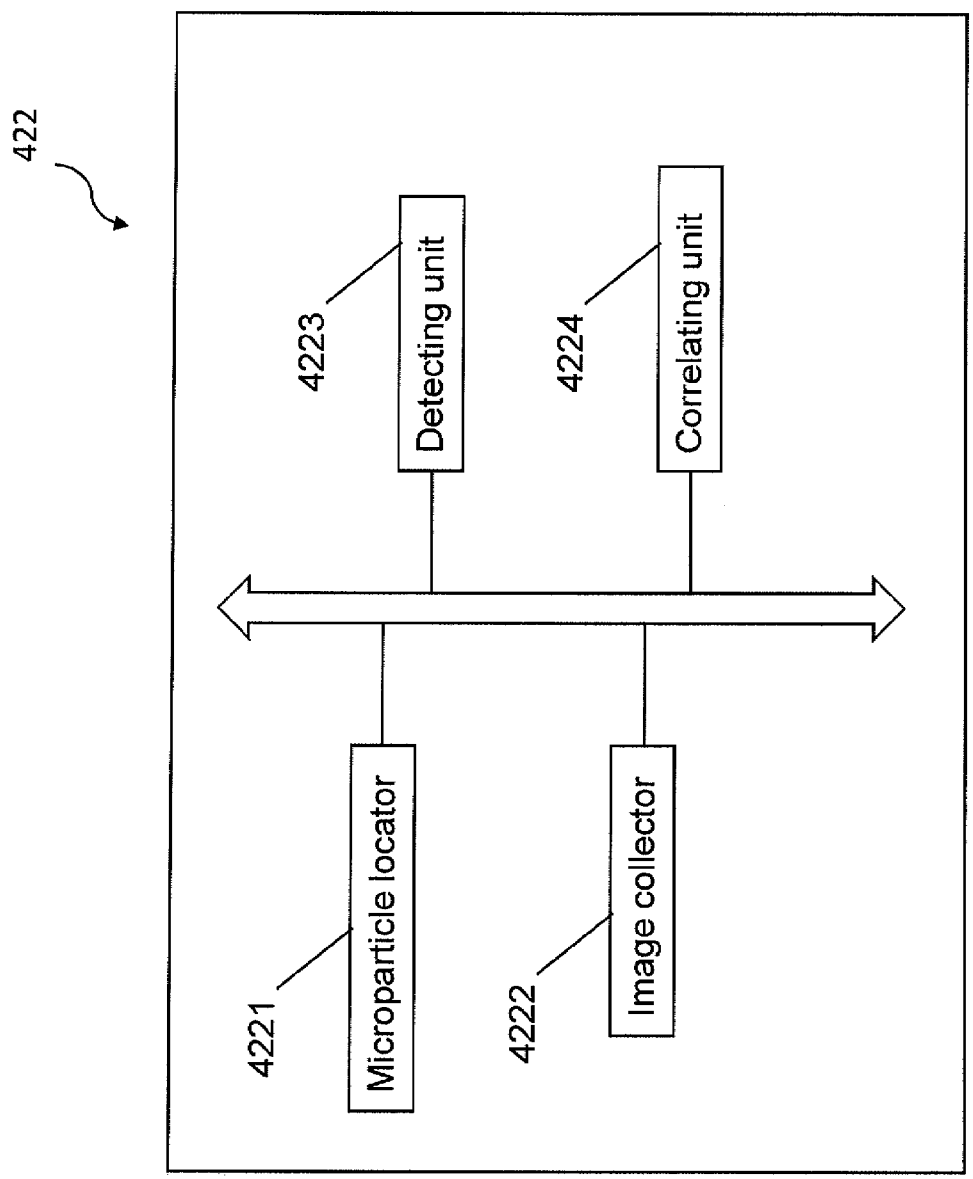
FIG. 4a illustrates one embodiment of the present invention shown in FIG. 4.

The system 400 in the present invention may further include a memory device 430 and a user interface 440, which may be operatively communicate with the computing device 420 to perform image optimization. In one embodiment illustrated in FIG. 4a, the processor 421 may include an initial image analyzer 422 configured for generating an initial function denoting each microparticle's location and intensity of the initial image, wherein the initial image analyzer 422 may include a microparticle locator 4221 for locating the microparticles in the initial image; a image collector 4222 for collecting images derived from scattered or focused light from said microparticles; a detecting unit 4223 for determining approximate center of each microparticle; and a correlating unit 4224 for correlating said intensities with the locations of said microparticles.

In another embodiment, the processor 420 may also include an optimum image generator 423 for computing an optimum function denoting each microparticle's location and intensity of an optimizing image; and producing the optimizing image with enhanced accuracy and density of the microparticles. The optimum image generator 423 may include means for finding the optimum function u in an $l_1$-minimization model (1) (described below); means for incorporating a weight function to provide location information of the microparticles; and means for inverting the extent of point spread and blurriness in the initial image.

Figure 5:
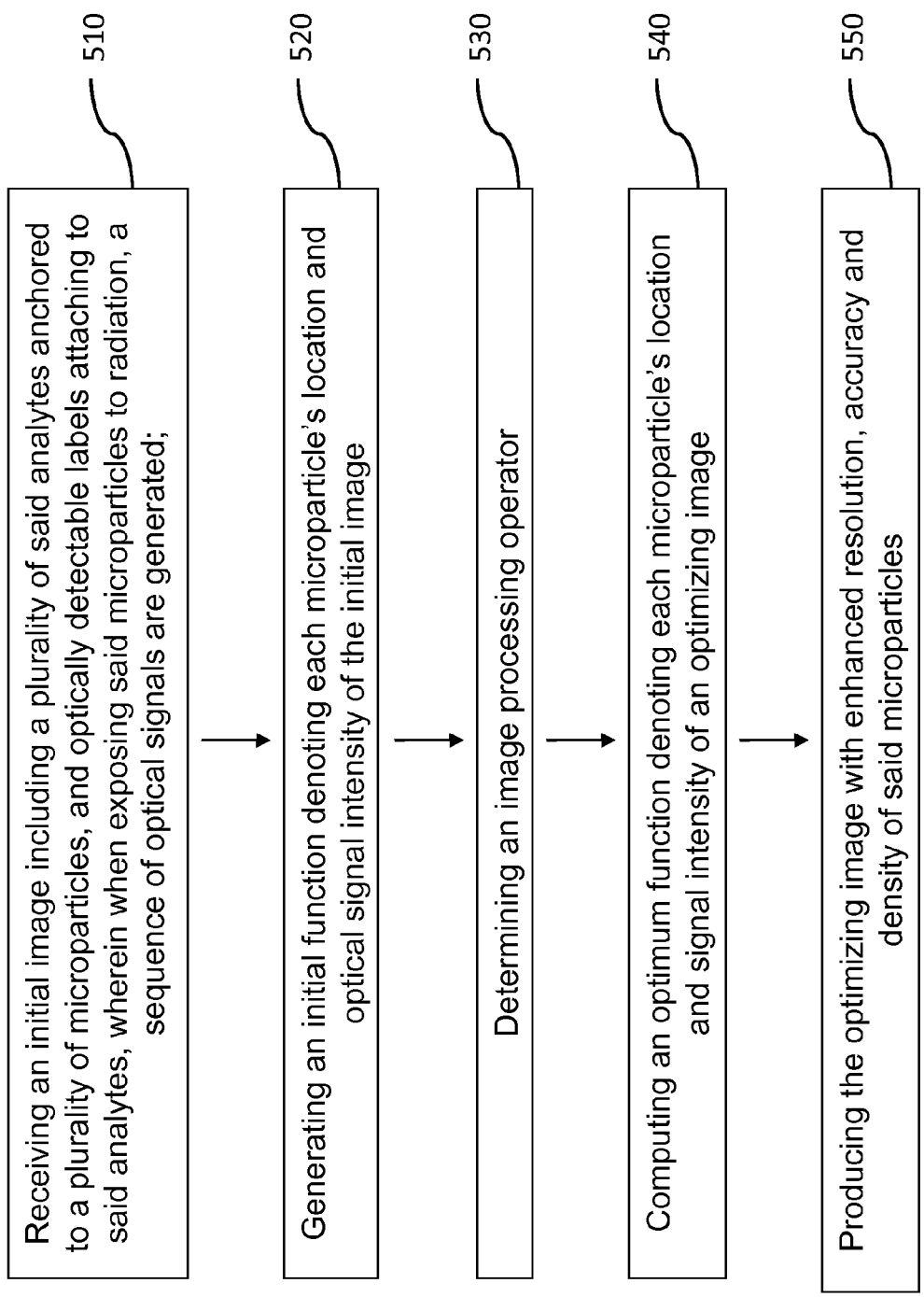
FIG. 5 depicts an exemplary aspect in the present invention, illustrating an image optimization method for generating an image with enhanced resolution, accuracy and density of the microparticles.

In an exemplary aspect of the present invention shown in FIG. 5, a method for optimizing images including a plurality of analytes anchored to a plurality microparticles comprises the steps of: receiving an initial image including a plurality of said analytes anchored to a plurality of microparticles and optically detectable labels attaching to said analytes 510, wherein when exposing said microparticles to radiation, a sequence of optical signals are generated; generating an initial function denoting each microparticle's location and optical signal intensity of the initial image 520; determining an image processing operator adapted to determine an extent of point spread and blurriness in the initial image 530; computing an optimum function denoting each microparticle's location and signal intensity of an optimizing image 540; and producing the optimizing image with enhanced resolution, accuracy and density of said microparticles 550, wherein the image processing operator is adapted to transform the optimum function to a modified optimum function, and when the difference of pixel values between the modified optimum function and the initial function is smaller than a predetermined threshold, the optimizing image is formed.

In one embodiment, the analytes may be oligonucleotides or nucleic acid molecules. In some embodiments, the microparticles may be the beads 210 shown in FIGS. 2, 2a and 2b, and the optical detectable label may be the dye molecule 230 in FIG. 2b. For DNA sequencing purposes, there may be four dye molecules with different wavelengths to distinguish four nucleobases: i.e., A, T, C, G.

In another embodiment, the step of receiving an initial image 510 may include the step of removing background, which can be implemented by the background removing unit 411. In a further embodiment, the initial image analyzer 422 can be used to implement the step of generating an initial function 520, wherein the initial image analyzer 422 may include a microparticle locator 4221 for locating the beads 210 in the initial image; a image collector 4222 for collecting images derived from scattered or focused light from said beads 210; a detecting unit 4223 for determining approximate center of each bead 210; and a correlating unit 4224 for correlating said intensities with the locations of said beads 210.

In an exemplary embodiment, the optimum image generator 423 can be used to implement the step of computing an optimum function 540, wherein the optimum image generator 423 may include means for finding the optimum function u in an $l_1$-minimization model (1) (described below); means for incorporating a weight function to provide location information of the microparticles; and means for inverting the extent of point spread and blurriness in the initial image.

EXPERIMENTS

Figure 6C:
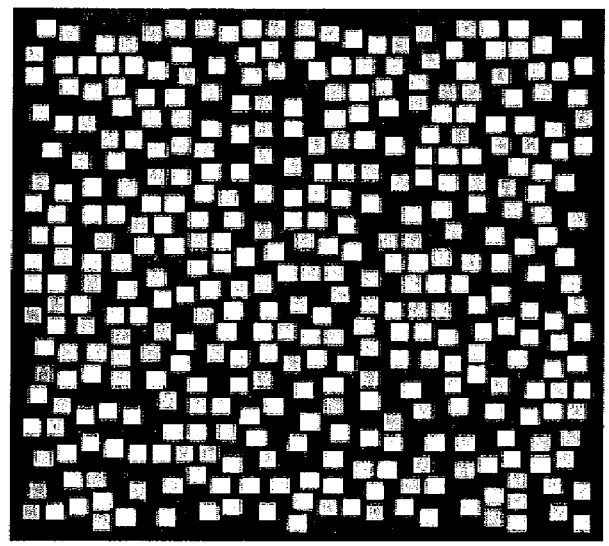
Figure 6B:
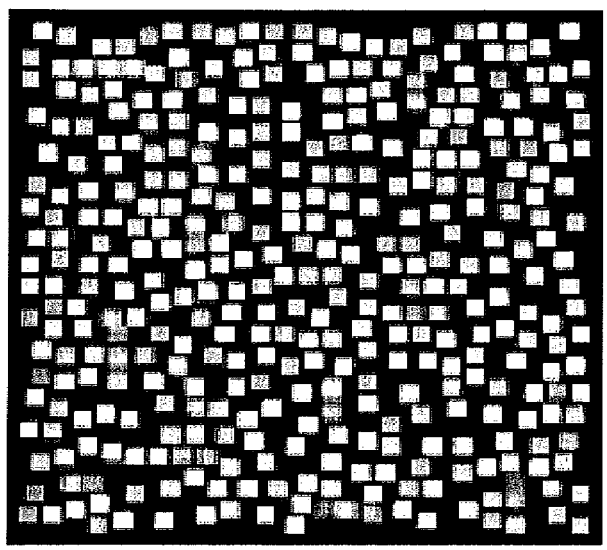
Figure 6A:
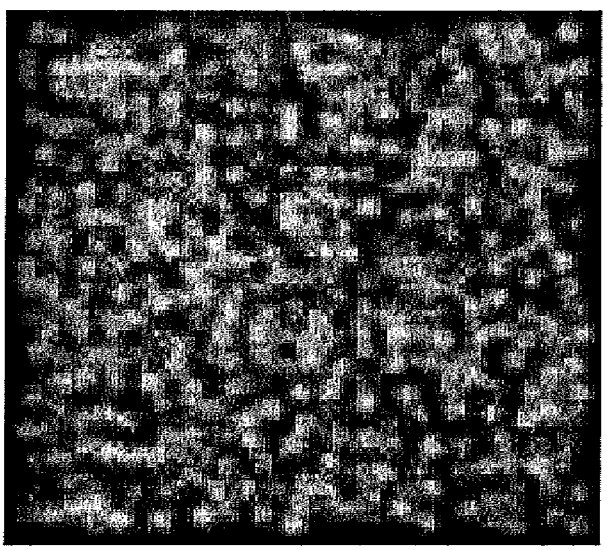
Figure 7A:
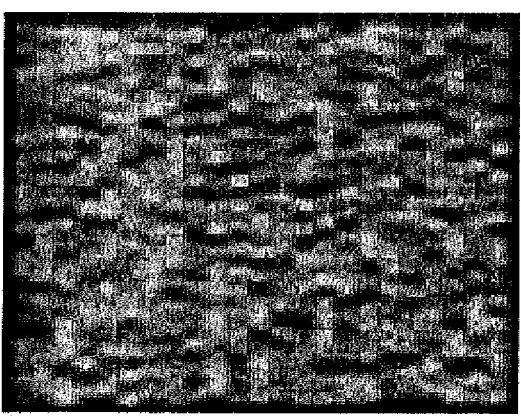

The mathematical model stated above is tested with synthetic images as depicted in FIGS. 6a and 7a, which contain artificial beads (3×3 squares) with random intensities. The synthetic images are processed, namely deblurred, by the abovementioned mathematical model. FIGS. 6b and 7b illustrate the deblurred images of FIGS. 6a and 7a, respectively, while FIGS. 6c and 7d illustrate the ground truth.

Moreover, in FIGS. 6a to 6c, the beads' locations are purely random, while in FIGS. 7a to 7d, the beads' location are only random along some known horizontal axes, which are used to determine the spatially variant threshold $\mu$. For example, $\mu$ can be large at the locations that are not along those horizontal axes. FIG. 7b illustrates the deblurred image (of FIG. 7a) with constant $\mu$, while FIG. 7c illustrates a deblurred image (of FIG. 7a) with spatial variant $\mu$ which can be closer to the ground truth shown in FIG. 7d.

Figure 8C:
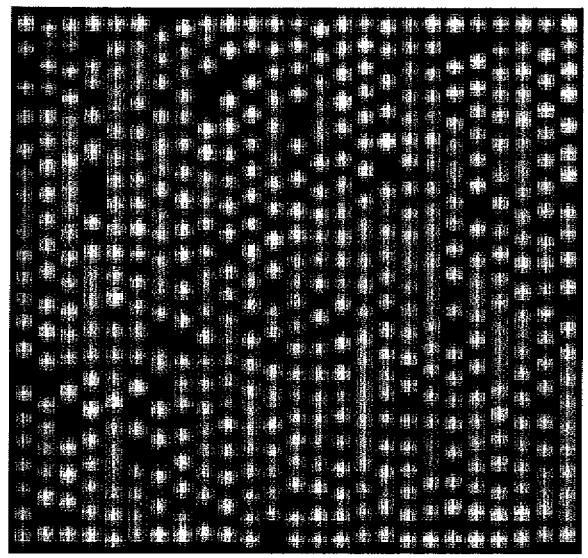
Figure 8B:
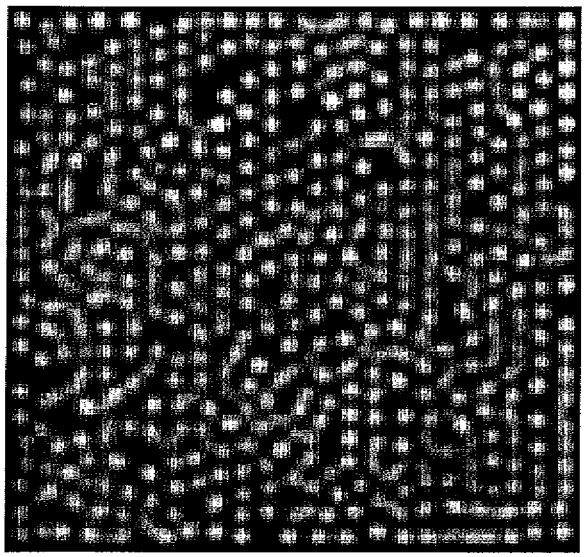
Figure 8A:
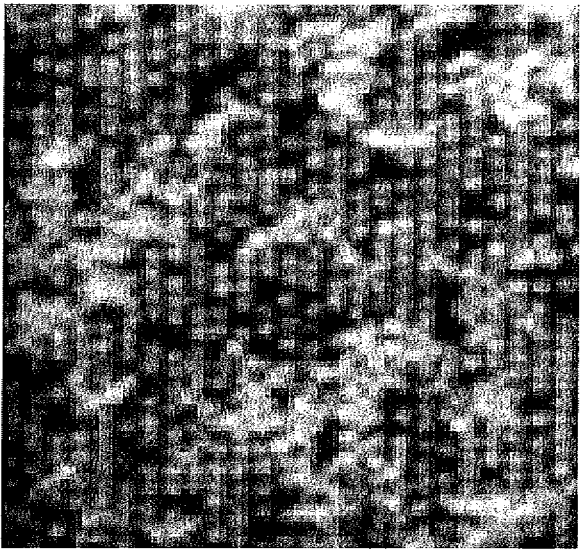

A further example to illustrate the application of the spatial variant $\mu$ can be seen in FIGS. 8a to 8c. A synthetic blurred image is shown in FIG. 8a. FIG. 8b illustrates a deblurred image by utilizing the abovementioned mathematical model with constant $\mu$, while FIG. 8c is the deblurred image with spatial variant $\mu$. Comparing FIG. 8b with 8c, with additional location information of the bead reflected by the spatial variant $\mu$, the deblurring result can be greatly improved.

Figure 9C:
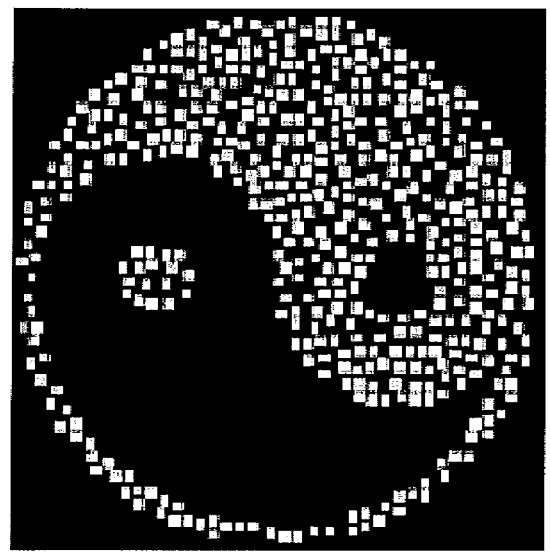
Figure 9B:
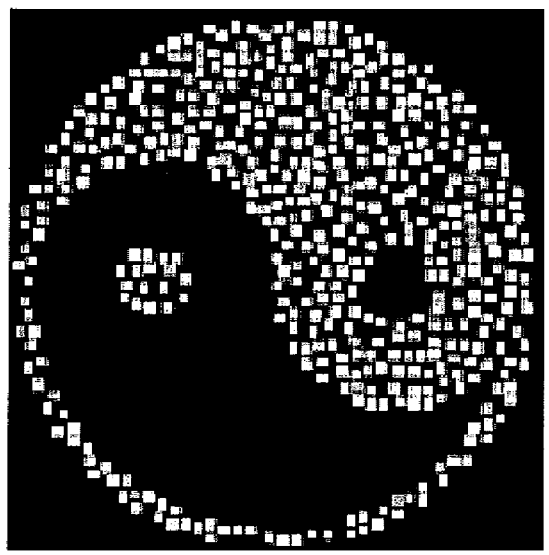
Figure 9A:
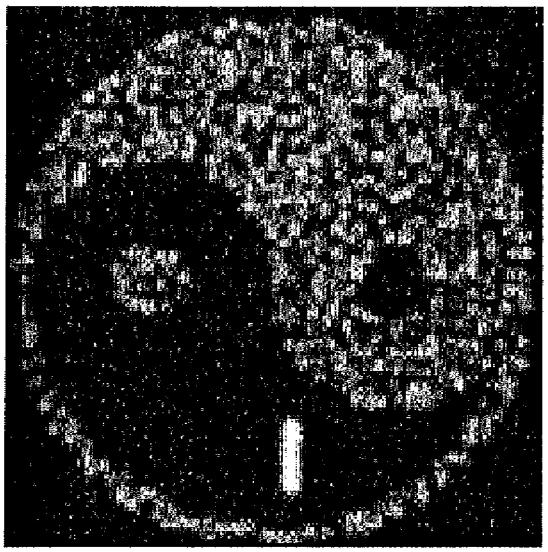

The image pattern can also be arbitrary as shown in FIGS. 9a to 9c, where the possible beads' locations are enclosed in a "Tai Ji" shaped region. Since there may be more beads located in certain areas than other areas in "Tai Ji," the spatial variant $\mu$ plays an even important role in the mathematical model. As can be seen in FIG. 9b, the spatial variant $\mu$ can be chosen to be relatively small inside and relatively large outside, so as to incorporate known location information of the patterns of the beads to better restore the image as FIG. 9c.

For implementing the mathematical model in real data, it may be necessary to remove the background before processing the image. The basic idea is to decompose the original image f as f=u+υ, where υ is the background. The following TV-$L_1$ model (S. Alliney. Digital filters as absolute norm regularizers. IEEE Trans. Signal Process., 40, 1548-1562, 1992; M. Nikolova. Minimizers of cost-functions involving nonsmooth data-fidelity terms, SIAM J. Numer. Anal., 40, 965-994, 2002; T. Chan and S. Esedoglu. Aspects of total variation regularized L1 function approximation. SIAM Journal on Applied Mathematics, 65(5), 1817-1837, 2005, which are incorporated herein by reference) may be used for background removal:

$$\min_{v \in R^2} \left\{ \int |\nabla v| + \lambda \|f - v\|_1 \right\} \qquad (4)$$

Figure 10A:
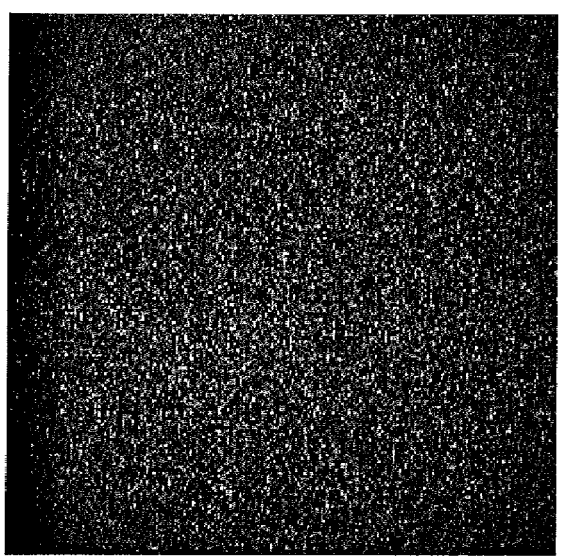
Figure 10B:
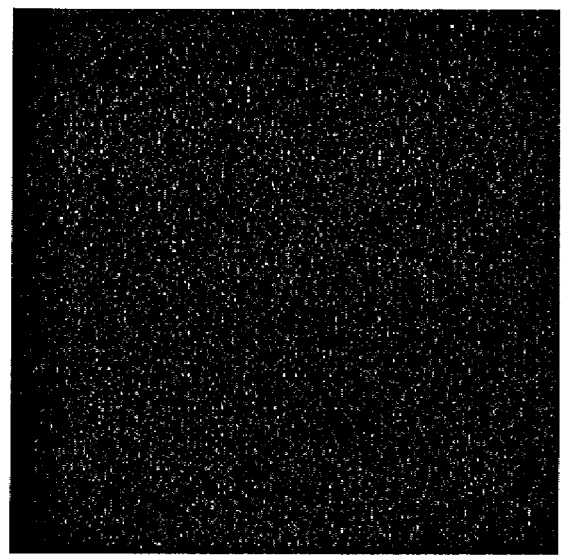
Figure 10C:
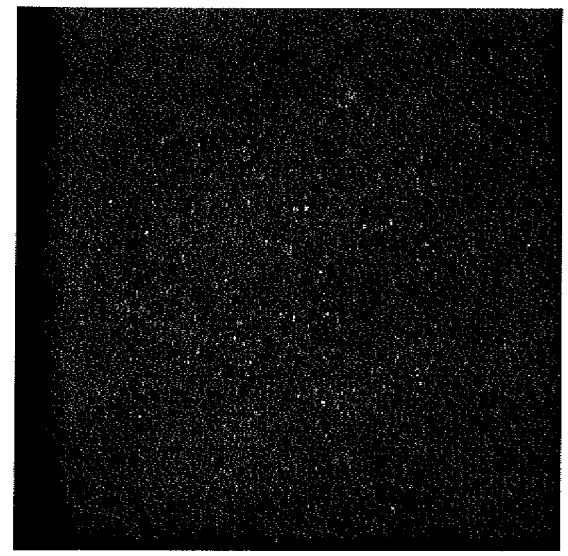

It is noted that there is an $L_1$ fidelity term instead of a traditional $L_2$ fidelity. To implement the minimization of (4), a super fast split Bregman iteration (Tom Goldstein and Stanley Osher, *The Split Bregman Algorithm for L1 Regularized Problems*, CAM-Report 08-29, April 2008, which is incorporated herein by reference) is applied to the $L_1$-fidelity problem (B. Dong, E. Savitsky and S. Osher, A Novel Method for Enhanced Needle Localization Using Ultrasound-Guidance, UCLA CAM-Report 08-65, September 2008, which is incorporated herein by reference). However, any other optimization routines can be used to solve this model (4). FIGS. 10a to 10c illustrate the result of background removal of Dye 1, where FIG. 10a shows the original image f, FIG. 10b shows background removal image u and FIG. 10c shows background υ.

However, the TV-$L_1$ model (4) does not work well for the image with all beads since the beads density of the focal map image is much higher than the image for each individual dyes, so that the sparsity assumption of u=f−υ, which is implicitly assumed by the $L_1$-fidelity, is violated. Thus, to remove the background of the focal map image, the following model (5) is used, which can be solved via Fast Fourier Transform (FFT):

$$\min_{v \in R^2} \left\{ \int |\nabla v|^2 + \frac{\mu}{2}\|f-v\|^2 + \lambda(v-f) \right\} \quad (5)$$

where $\mu$ and $\lambda$ are nonnegative parameters that can be easily tuned experimentally. FIGS. 11a to 11c depict the result for background removal of the focal map images, where FIG. 11a illustrates the original image f, while FIGS. 11b and 11c illustrate the background removed image u, and background image υ, respectively. It is noted that the procedure for deblurring the real beads images shown above is to first apply the background removal models (4) and (5), and then solve the $l_1$-minimization model (1).

In some embodiments, a registration technique may be used when images taken at different times, or from different perspectives, are compared or integrated with each other. For example, according to the locations of the beads given by the focal map image, the registration technique may be necessary to read the signal from the images of Dye 1 to Dye 4. Since these images are only differ by translations, a correlation function between f and g can be used:

$$\hat{h} := \hat{f}\overline{\hat{g}}$$

where f is the template image; g is the image which needs to be matched to f; $\hat{f}$ and $\hat{g}$ denote the Fourier transforms of f and g; and $\overline{\hat{g}}$ denotes the complex conjugate of $\hat{g}$.

Figure 12A:
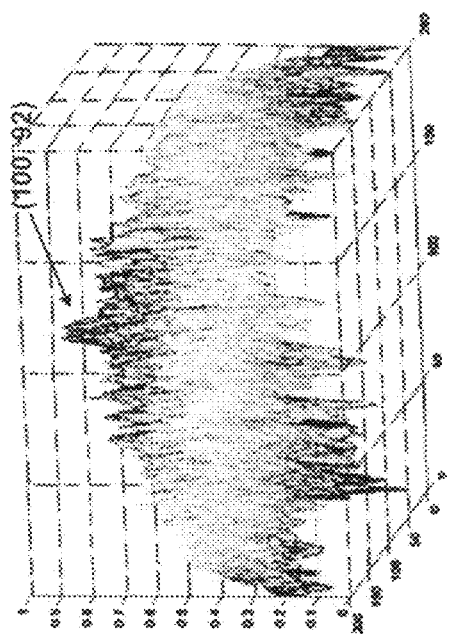
Figure 12B:
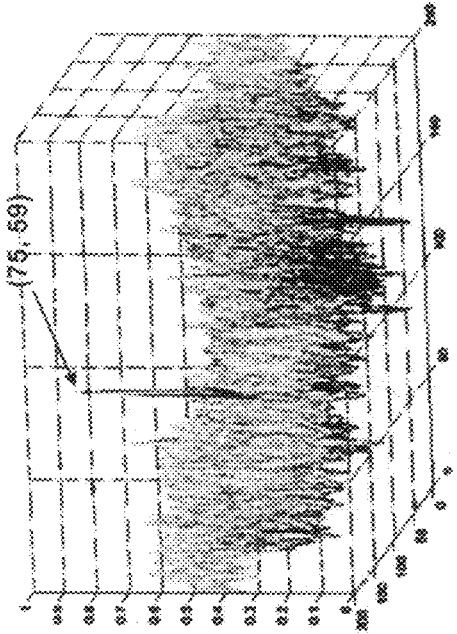
Figure 12C:
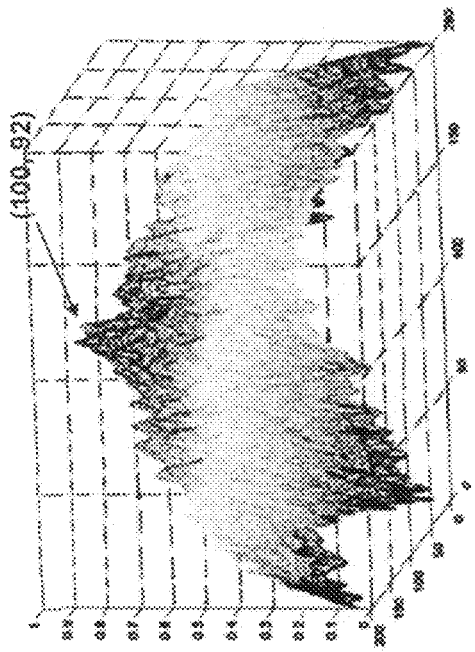
Figure 12D:
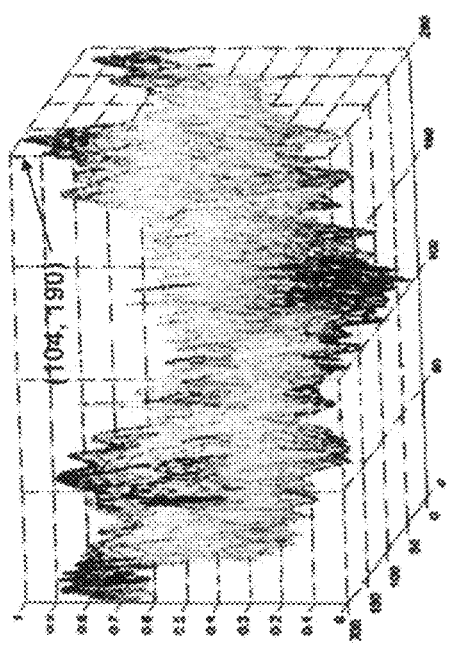

In one experiment, f can be chosen as the center 200×200 patch of the image with all beads, and g can be chosen as the center 100×100 patch of the image of Dye 4. Here, it is known the ground truth is that the (1, 1) of g corresponds to (25, 9) of f, which is justified manually. Therefore, the correct location of the peak of h should be (75, 59). It is noted that using deblurred images f and g, the correct translation can be accurately detected as shown in FIG. 12d, while the same translation may not be detected if at least one image is not deblurred, as shown in FIGS. 12a to 12c.

Having described the invention by the description and illustrations above, it should be understood that these are exemplary of the invention and are not to be considered as limiting. Accordingly, the invention is not to be considered as limited by the foregoing description, but includes any equivalents.

The invention claimed is:

1. An image optimization method, comprising the steps of:
receiving an initial image which includes a plurality of microparticles with different intensities;
generating an initial function denoting each microparticle's location and intensity in the initial image;
determining an image processing operator to determine an extent of point spread and blurriness in the initial image;
computing an optimum function denoting each microparticle's location and intensity in an optimizing image; and
producing the optimizing image with enhanced resolution, accuracy and density of said microparticles,
wherein the image processing operator is adapted to transform the optimum function to a modified optimum function, and when the difference of pixel values between the modified optimum function and the initial function is smaller than a predetermined threshold, the optimizing image is formed.

2. The method of claim 1, wherein the step of receiving an initial image includes the step of removing background in said initial image.

3. The method of claim 1, wherein the step of generating an initial function denoting each microparticle's location and signal intensity in the initial image includes the step of locating the microparticles in the initial image; collecting images derived from scattered or focused light from said microparticles; determining approximate center of each microparticle; and correlating said sequence of said optical signals with the locations of said microparticles.

4. The method of claim 1, wherein the step of computing an optimum function denoting each microparticle's location and intensity in an optimizing image includes the step of finding said optimum function u in an $l_1$-minimization model as:

$$\min_u \left\{ \|\mu u\|_1 + \frac{1}{2\delta}\|u\|^2 \text{ s.t. } \|Au - f\| \le \varepsilon \right\}.$$

5. The method of claim 4, wherein the step of computing an optimum function denoting each microparticle's location and intensity in an optimizing image includes the step of incorporating a weight function to provide location information of the microparticles.

6. The method of claim 5, wherein the step of computing an optimum function denoting each microparticle's location and intensity in an optimizing image includes the steps of inverting the extent of point spread and blurriness in the initial image.

7. A system for optimizing an image, comprising:
means for receiving an initial image which includes a plurality of microparticles with different intensities;
a computing device, comprising
a processor executing instructions to perform:
generating an initial function denoting each microparticle's location and intensity in the initial image;
determining an image processing operator adapted to determine an extent of point spread and blurriness in the initial image;
computing an optimum function denoting each microparticle's location and intensity in an optimizing image; and
producing the optimizing image with enhanced resolution, accuracy and density of the microparticles,
wherein the image processing operator is adapted to transform the optimum function to a modified optimum function, and when the difference of pixel values in the modified optimum function and the initial function is smaller than a predetermined threshold, the optimizing image is formed.

8. The system of claim 7, wherein the means for receiving an initial image includes means for removing background in said initial image.

9. The system of claim 7, wherein generating an initial function denoting each microparticle's location and intensity in the initial image includes locating the microparticles in the initial image; collecting images derived from scattered or focused light from said microparticles; determining approximate center of each microparticle; and correlating said intensities with the locations of said microparticles.

10. The system of claim 7, wherein computing an optimum function denoting each microparticle's location and intensity in an optimizing image includes finding said optimum function u in an $l_1$-minimization model as:

$$\min_u \left\{ \|\mu u\|_1 + \frac{1}{2\delta}\|u\|^2 \text{ s.t. } \|Au - f\| \le \varepsilon \right\}.$$

11. The system of claim 10, wherein computing an optimum function denoting each microparticle's location and intensity in an optimizing image includes incorporating a weight function to provide location information of said microparticles.

12. The method of claim 11, wherein computing an optimum function denoting each particle's location and intensity in an optimizing image includes inverting the extent of point spread and blurriness in the initial image.

13. A method for optimizing an image including a plurality of analytes anchored to a plurality microparticles, comprising the steps of:
receiving an initial image including a plurality of said analytes anchored to a plurality of microparticles, and optically detectable labels attaching to said analytes, wherein when exposing said microparticles to radiation, a sequence of optical signals are generated;
generating an initial function denoting each microparticle's location and optical signal intensity in the initial image;
determining an image processing operator adapted to determine an extent of point spread and blurriness in the initial image;
computing an optimum function denoting each microparticle's location and signal intensity in an optimizing image; and
producing the optimizing image with enhanced resolution, accuracy and density of said microparticles,
wherein the image processing operator is adapted to transform the optimum function to a modified optimum function, and when the difference of pixel values between the modified optimum function and the initial function is smaller than a predetermined threshold, the optimizing image is formed.

14. The method of claim 13, wherein the step of receiving an initial image includes the step of removing background in said initial image.

15. The method of claim 13, wherein the step of generating an initial function denoting each microparticle's location and signal intensity in the initial image includes the step of locating the microparticles in the initial image; collecting images derived from scattered or focused light from said microparticles; determining approximate center of each microparticle; and correlating said sequence of said optical signals with the locations of said microparticles.

16. The method of claim 13, wherein the step of computing an optimum function denoting each microparticle's location and intensity in an optimizing image includes the step of finding said optimum function u in an $l_1$-minimization model as:

$$\min_u \left\{ \|\mu u\|_1 + \frac{1}{2\delta}\|u\|^2 \text{ s.t. } \|Au - f\| \le \varepsilon \right\}.$$

17. The method of claim 16, wherein the step of computing an optimum function denoting each microparticle's location and intensity in an optimizing image includes the step of incorporating a weight function to provide location information of the microparticles.

18. The method of claim 17, wherein the step of computing an optimum function denoting each particle's location and intensity in an optimizing image includes the step of inverting the extent of point spread and blurriness in the initial image.

19. The method of claim 13, wherein said analytes are oligonucleotides or nucleic acid molecules.

* * * * *

SEQUENCE LISTING

```
<160> NUMBER OF SEQ ID NOS: 5

<210> SEQ ID NO 1
<211> LENGTH: 28
<212> TYPE: DNA
<213> ORGANISM: Artificial Sequece
<220> FEATURE:
<223> OTHER INFORMATION: Exemplary sequence intended to illustrate
      current DNA sequencing process

<400> SEQUENCE: 1
attagttgat tacatcggtg cggactag                                          28

<210> SEQ ID NO 2
<211> LENGTH: 7
<212> TYPE: DNA
<213> ORGANISM: Artificial Sequence
<220> FEATURE:
<223> OTHER INFORMATION: Exemplary sequence intended to illustrate
      current DNA sequencing process

<400> SEQUENCE: 2 attagtt                                                                  7

<210> SEQ ID NO 3
<211> LENGTH: 7
<212> TYPE: DNA
<213> ORGANISM: Artificial Sequence
<220> FEATURE:
<223> OTHER INFORMATION: Exemplary sequence intended to illustrate
      current DNA sequencing process

<400> SEQUENCE: 3 gattaca                                                                  7

<210> SEQ ID NO 4
<211> LENGTH: 7
<212> TYPE: DNA
<213> ORGANISM: Artificial Sequence
<220> FEATURE:
```

-continued

```
<223> OTHER INFORMATION: Exemplary sequence intended to illustrate
      current DNA sequencing process

<400> SEQUENCE: 4 tcggtgc                                                                7

<210> SEQ ID NO 5
<211> LENGTH: 7
<212> TYPE: DNA
<213> ORGANISM: Artificial Sequence
<220> FEATURE:
<223> OTHER INFORMATION: Exemplary sequence intended to illustrate
      current DNA sequencing process

<400> SEQUENCE: 5 ggactag                                                                7
```